(12) United States Patent
Enomura et al.

(10) Patent No.: US 11,629,063 B2
(45) Date of Patent: Apr. 18, 2023

(54) METHOD OF PRODUCING ULTRAVIOLET PROTECTIVE AGENT COMPOSITION, AND ULTRAVIOLET PROTECTIVE AGENT COMPOSITION OBTAINED THEREBY

(71) Applicant: M. TECHNIQUE CO., LTD., Izumi (JP)

(72) Inventors: Masakazu Enomura, Izumi (JP); Daisuke Honda, Izumi (JP)

(73) Assignee: M. TECHNIQUE CO., LTD., Izumi (JP)

( * ) Notice: Subject to any disclaimer, the term of this patent is extended or adjusted under 35 U.S.C. 154(b) by 19 days.

(21) Appl. No.: 15/559,342

(22) PCT Filed: Jun. 24, 2016

(86) PCT No.: PCT/JP2016/068806
§ 371 (c)(1),
(2) Date: Sep. 18, 2017

(87) PCT Pub. No.: WO2016/208715
PCT Pub. Date: Dec. 29, 2016

(65) Prior Publication Data
US 2018/0111842 A1    Apr. 26, 2018

(30) Foreign Application Priority Data

Jun. 26, 2015   (JP) .............................. JP2015-129279

(51) Int. Cl.
*C01G 49/06*       (2006.01)
*C09C 1/24*        (2006.01)
(Continued)

(52) U.S. Cl.
CPC ................ *C01G 49/06* (2013.01); *A61K 8/04* (2013.01); *A61K 8/19* (2013.01); *A61Q 17/04* (2013.01);
(Continued)

(58) Field of Classification Search
CPC .. C01G 49/06; C09C 1/24; C09D 5/32; C09D 7/67; C30B 7/14; C30B 29/16; C01P 2004/64; C01P 2006/60; G02B 5/208
See application file for complete search history.

(56) References Cited

U.S. PATENT DOCUMENTS

| | | | |
|---|---|---|---|
| 2002/0071948 A1* | 6/2002 | Duff ........................ | B82Y 30/00 428/323 |
| 2009/0029172 A1* | 1/2009 | Isozaki ................... | A61L 27/18 428/412 |

(Continued)

FOREIGN PATENT DOCUMENTS

| | | |
|---|---|---|
| JP | 2-178219 A | 7/1990 |
| JP | 2-271925 A | 11/1990 |

(Continued)

OTHER PUBLICATIONS

K. Raja, M. Mary Jaculine M. Jose, Sunil Verma, A.A.M. Prince, K. Ilangovan, K. Sethusankar, S. Jerome Das, Sol-gel synthesis and characterization of α-Fe2O3 nanoparticles, Superlattices and Microstructures, 86, 2015, 306-312. (Year: 2015).*

(Continued)

*Primary Examiner* — Bijan Ahvazi
(74) *Attorney, Agent, or Firm* — Birch, Stewart, Kolasch & Birch, LLP

(57) ABSTRACT

A method of producing an ultraviolet protective agent composition, which has high transparency and excellent protection ability against a light of ultraviolet region of wavelengths of 200 to 420 nm, and an ultraviolet protective agent composition obtained by the production method are provided. The method of producing an ultraviolet protective agent composition includes at least step (a) of precipitating iron oxide microparticles by mixing with a microreactor an iron oxide raw material fluid containing at least $Fe^{3+}$ ion, and an iron oxide precipitation fluid containing at least a basic (Continued)

substance; and step (b) of dispersing the above precipitated iron oxide microparticles in a dispersion medium to obtain iron oxide microparticle dispersion, wherein a haze value of the iron oxide microparticle dispersion is 2.0% or less, and a transmittance of the iron oxide microparticle dispersion for the light of the wavelengths of 200 to 420 nm is 2.0% or less.

17 Claims, 13 Drawing Sheets

(51) Int. Cl.
    *C09D 7/40*     (2018.01)
    *G02B 5/20*     (2006.01)
    *A61Q 17/04*     (2006.01)
    *A61K 8/19*     (2006.01)
    *A61K 8/04*     (2006.01)
    *C09K 3/00*     (2006.01)
    *C09D 5/32*     (2006.01)
    *C30B 7/14*     (2006.01)
    *C30B 29/16*     (2006.01)

(52) U.S. Cl.
    CPC .................. *C09C 1/24* (2013.01); *C09D 5/32* (2013.01); *C09D 7/67* (2018.01); *C09K 3/00* (2013.01); *C30B 7/14* (2013.01); *C30B 29/16* (2013.01); *G02B 5/208* (2013.01); *C01P 2004/64* (2013.01); *C01P 2006/60* (2013.01)

(56) References Cited

U.S. PATENT DOCUMENTS

| | | | | |
|---|---|---|---|---|
| 2009/0311295 | A1* | 12/2009 | Mathiowitz | A61K 8/11 264/4.6 |
| 2010/0155310 | A1* | 6/2010 | Enomura | B01F 3/0807 209/668 |
| 2010/0239620 | A1* | 9/2010 | Butler | C09D 11/037 106/31.13 |
| 2012/0269896 | A1* | 10/2012 | Hakata | A61K 41/0052 424/497 |
| 2013/0156682 | A1 | 6/2013 | Kuraki et al. | |
| 2015/0283552 | A1* | 10/2015 | Chartoff | B03C 1/01 209/8 |
| 2015/0321154 | A1 | 11/2015 | Enomura | |

FOREIGN PATENT DOCUMENTS

| | | | | |
|---|---|---|---|---|
| JP | 4-114725 | A | | 4/1992 |
| JP | 5-319832 | A | | 12/1993 |
| JP | 2005-145805 | A | | 6/2005 |
| JP | 2008-194563 | A | | 8/2008 |
| JP | 2008-231164 | A | | 10/2008 |
| JP | 2009-57419 | A | | 3/2009 |
| JP | 2009057419 | A | * | 3/2009 ............ B32B 27/00 |
| JP | 2009-132596 | A | | 6/2009 |
| JP | 5147091 | B1 | | 2/2013 |
| JP | 2013-82621 | A | | 5/2013 |
| JP | 2014-169234 | A | | 9/2014 |
| WO | WO 2006/087880 | A1 | | 8/2006 |
| WO | WO 2009/008393 | A1 | | 1/2009 |

OTHER PUBLICATIONS

Extended European Search Report, dated Dec. 7, 2018, for European Application No. 16814484.8.
International Search Report, issued in PCT/JP2016/068806, dated Sep. 13, 2016.
Korean Office Action, dated May 23, 2019, for Korean Application No. 10-2017-7031744, along with an English translation.
Chinese Office Action and Search Report for Chinese Application No. 201680021992.3, dated Jul. 3, 2020, with an English translation.

* cited by examiner

METHOD OF PRODUCING ULTRAVIOLET PROTECTIVE AGENT COMPOSITION, AND ULTRAVIOLET PROTECTIVE AGENT COMPOSITION OBTAINED THEREBY

TECHNICAL FIELD

The present invention relates to a method of producing an ultraviolet protective agent composition, and an ultraviolet protective agent composition obtained thereby.

BACKGROUND ART

An ultraviolet protective agent composition is used in the optical field or a medical material, or in a resin composition used in the electrical and electronic fields, or in a sunscreen in the cosmetics field, or in various paints or the like. When used as cosmetics, transparency and safety are important in addition to the ultraviolet protection ability, for direct application to the skin. When used as a paint, the composition is used normally to protect against effect of ultraviolet rays on a color material such as a paint used in a separate foundation, and a pigment used in the paint and the like. Therefore, the ultraviolet protection ability as well as transmittance of a light other than ultraviolet ray, in particular a visible light are important. That is, for an ultraviolet protective agent composition, an ability to absorb or shield ultraviolet rays as well as transparency are required.

As an ultraviolet protective agent composition, Patent Literature 1 discloses an ultraviolet shielding agent comprising an anatase type titanium oxide having an average particle size of 0.6 to 0.8 μm and an iron oxide, and cosmetics containing the same. Patent Literature 2 discloses a transparent thermoplastic resin composition of a haze value of 3% or less with an absorbing ability to a light of the wavelength of 420 nm or less, by containing an ultraviolet absorber such as iron oxide/titanium oxide having an average primary particle diameter of 10 to 80 nm, a benzotriazole compound or a benzoate compounds. Further, Patent Literature 3 discloses a method of producing α-ferric oxide of 0.01 to 0.06 μm, having excellent dispersibility, ultraviolet shielding property and transparency, which surface is coated by a polyhydric alcohol and an organosiloxane, and a thermoplastic resin molded product.

However, in the ultraviolet protective agent composition as described in Patent Literature 1, since a large particle size of titanium oxide or iron oxide is used to shield an ultraviolet ray, it is difficult to ensure transparency of the ultraviolet protective agent composition. Moreover, ultraviolet absorbing ability and transparency of the wavelength of 420 nm by the ultraviolet protective agent composition described in Patent Literature 2 are insufficient, and in addition, since protection against a light of the wavelength up to about 420 nm only by iron oxide/titanium oxide is insufficient, it is necessary to use an organic material such as a benzotriazole compound and a benzoate compound which is inferior in durability compared with an inorganic compound, and thus, the ultraviolet protective agent composition described in Patent Literature 2 has poor stability and difficulty in a long time of use. Further, a thermoplastic resin molded product using the α-ferric oxide produced by the method of Patent Literature 3 has insufficient transparency, and in addition, as described in Patent Literature 2, it is necessary for improving the dispersibility to coat the α-ferric oxide surface with an organic compound such as a polyhydric alcohol and an organosiloxane which is inferior in durability compared with an inorganic compound, and thus, the thermoplastic resin molded product of Patent Literature 3 has poor stability and difficulty in a long time of use. Although Patent Literature 3 describes α-ferric oxide which surface is coated with a polyhydric alcohol and an organosiloxane, and a method of producing a thermoplastic resin molded product in which the α-ferric oxide is dispersed, it does not describe a method of producing α-ferric oxide microparticles themselves.

Patent Literature 4 filed by the present applicant discloses a method of producing a titanium dioxide supermicroparticles by precipitating microparticles of titanium dioxide between two processing surfaces being capable of approaching to and separating from each other and rotating relative to each other. Patent Literature 5 filed by the present applicant discloses a method of producing various nanoparticles of iron oxides and the like. However, the titanium dioxide supermicroparticles produced by the method described in Patent Literature 4, similarly to conventional titanium dioxide microparticles, have high absorbing ability of so-called UVB of the ultraviolet wavelength of 290 to 320 nm, but poor absorbing ability of so-called UVA of the ultraviolet wavelength longer than 320 nm, particularly up to 420 nm. Moreover, the iron oxide nanoparticles described in Patent Literature 5 are the nanoparticles of black iron oxide ($Fe_3O_4$: magnetite) and yellow iron oxide (FeOOH: goethite), and it was not observed that these iron oxide nanoparticles have ultraviolet absorbing ability of a wavelength up to 420 nm.

CITATION LIST

Patent Literature

Patent Literature 1: JP 2014-169234
Patent Literature 2: WO 2006/087880
Patent Literature 3: JP 2005-145805
Patent Literature 4: JP 2009-132596
Patent Literature 5: WO 2009/008393

SUMMARY OF THE INVENTION

Technical Problem

In light of such circumstances, the present invention is intended to provide a method of producing an ultraviolet protective agent composition, wherein a haze value of the iron oxide particle dispersion is 2.0% or less, and a transmittance for the light of the wavelengths of 200 to 420 nm is 2.0% or less, and an ultraviolet protective agent composition obtained by the production method.

The present inventors have made intensive studies to solve the above problems, and found that the above problems can be achieved by the production method described below, and have completed the present invention.

Solution to the Problem

The present invention is a method of producing an ultraviolet protective agent composition, which comprises at least step (a) of precipitating iron oxide microparticles by mixing with a microreactor an iron oxide raw material fluid containing at least $Fe^{3+}$ ion, and an iron oxide precipitation fluid containing at least a basic substance; and step (b) of dispersing the above precipitated iron oxide microparticles in a dispersion medium to obtain iron oxide microparticle dispersion; wherein a haze value of the iron oxide microparticle dispersion is 2.0% or less, and a transmittance of the iron oxide microparticle dispersion for the light of the wavelengths of 200 to 420 nm is 2.0% or less.

The present invention is also a method of producing an ultraviolet protective agent composition, wherein a transmittance of the iron oxide microparticle dispersion for the light of the wavelengths of 650 to 800 nm is 80% or more.

The present invention is also a method of producing an ultraviolet protective agent composition, wherein a primary particle diameter of the iron oxide microparticles is less than 25 nm.

The present invention is also a method of producing an ultraviolet protective agent composition, wherein a secondary particle diameter of the iron oxide microparticles is 50 nm or less.

The present invention is also a method of producing an ultraviolet protective agent composition, wherein a molar absorption coefficient of the iron oxide microparticle dispersion for the light of the wavelength of 400 nm is 500 L/(mol·cm) or more, and a molar absorption coefficient of the iron oxide microparticle dispersion for the light of the wavelength of 220 nm is 3000 L/(mol·cm) or more.

The present invention is also a method of producing an ultraviolet protective agent composition, wherein the iron oxide microparticles comprise substantially spherical iron oxide microparticles. The present invention is also a method of producing an ultraviolet protective agent composition, wherein the iron oxide microparticles comprise single crystals of iron oxide microparticles.

The present invention is also a method of producing an ultraviolet protective agent composition, wherein the iron oxide is α-hematite.

The present invention provides a method of producing an ultraviolet protective agent composition, wherein as a microreactor is used a fluid processing machine equipped with the first processing surface and the second processing surface which are disposed so as to face each other, being capable of approaching to and separating from each other, at least one of which rotates relatively to the other. According to this production method, at least two kinds of fluids to be processed of the iron oxide raw material fluid and the iron oxide precipitation fluid are introduced between the first processing surface and the second processing surface. Thereby, a separation force acting in the direction of separating the first processing surface and the second processing surface is generated by an introduction pressure of the fluids to be processed, so that the interval between the first processing surface and the second processing surface is maintained minute by a pressure balance between the separation force and the force applied in the direction of approximating the first processing surface and the second processing surface. The at least two fluids to be processed are merged between the first processing surface and the second processing surface which are maintained with the minute interval, and are passed between the first processing surface and the second processing surface, to form a thin film fluid. The fluids to be processed are mixed in the thin film fluid to precipitate the iron oxide microparticles. The method of producing an ultraviolet protective agent composition of the present invention is characterized by these steps.

It is preferable to introduce the iron oxide raw material fluid to be mixed between the processing surfaces, between the processing surfaces at the temperature of or higher than the normal boiling point of the iron oxide raw material fluid. In particular, an ultraviolet protective agent composition wherein a haze value is 2.0% or less, and a transmittance for the light of the wavelengths of 200 to 420 nm is 2.0% or less, can be produced, when the introduction pressure of both the fluids to be processed of the iron oxide raw material fluid and the iron oxide precipitation fluid exceeds the standard pressure, and the temperature of the iron oxide raw material fluid to be introduced between the processing surfaces is higher than the normal boiling point of the iron oxide raw material fluid, and is lower than the boiling point under the introduction pressure.

The present invention provides a method of producing an ultraviolet protective agent composition comprising step (a-2) of performing an additional stirring treatment to the discharged fluid to be processed, after discharging the fluid to be processed from the space between the processing surfaces and before step (b). More stable effective ultraviolet protective agent composition can be produced by making pH of the fluid discharged in step (a) or pH of the fluid obtained in step (a-2) be 6 to 14.

The present invention provides an ultraviolet protective agent composition obtained by a method of producing an ultraviolet protective agent composition described above.

An ultraviolet protective agent composition of the present invention is an ultraviolet protective agent composition which may be obtained by precipitating iron oxide microparticles by mixing with a microreactor an iron oxide raw material fluid containing at least $Fe^{3+}$ ion, and an iron oxide precipitation fluid containing at least a basic substance, followed by dispersing the above precipitated iron oxide microparticles in a dispersion medium; wherein a primary particle diameter of the iron oxide microparticles is less than 25 nm, and more than 90% of the iron oxide microparticles is single crystals; and wherein a haze value of the iron oxide microparticle dispersion is 2.0% or less, and a transmittance of the iron oxide microparticle dispersion for the light of the wavelengths of 200 to 420 nm is 2.0% or less.

Iron oxide microparticles are preferably microparticles obtained using a fluid processing machine equipped with the first processing surface and the second processing surface which are disposed so as to face each other, being capable of approaching to and separating from each other, at least one of which rotates relatively to the other.

In particular, the iron oxide raw material fluid to be mixed between the processing surfaces is preferably introduced into the space between the processing surfaces at a temperature of or higher than the normal boiling point of the iron oxide raw material fluid. Further, it is preferable that the introduction pressure of both the fluids to be processed of the iron oxide raw material fluid and the iron oxide precipitation fluid exceeds the standard pressure, and the temperature of the iron oxide raw material fluid to be introduced between the processing surfaces is higher than the normal boiling point of the iron oxide raw material fluid, and is lower than the boiling point under the introduction pressure.

Further, preferred are particles obtained by making the pH of the discharged fluid to be processed be 6 to 14, more preferably 8 to 12. In case of performing an additional stirring treatment to the discharged fluid to be processed, preferred are microparticles obtained by making the pH of the stirred fluid to be processed be 6 to 14, more preferably 8 to 12.

Advantageous Effects of the Invention

The production method of the present invention can provide an ultraviolet protective agent composition having high transparency and excellent protective ability against the ultraviolet region, which is an iron oxide microparticle dispersion.

Further, the present invention can provide an ultraviolet protective agent composition having high transparency and excellent protective ability against the ultraviolet region.

DESCRIPTION OF THE INVENTION

Figure 1:
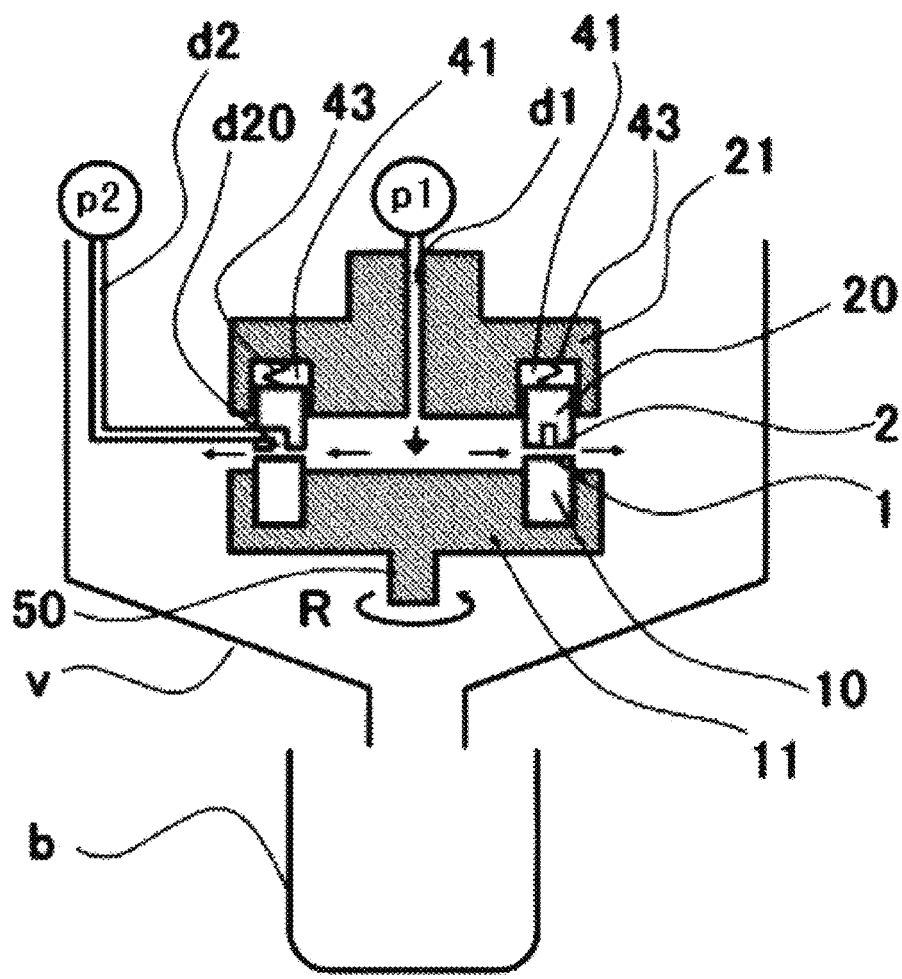
FIG. 1 shows an approximate cross sectional view of a fluid processing machine according to the embodiment of the present invention.

Hereinafter, embodiments of the present invention is described in detail. Incidentally, the present invention is not limited only to the embodiments described hereinafter.

The present invention is a method of producing an ultraviolet protective agent composition comprising at least step (a) and step (b).

Step (a) is a step of precipitating iron oxide microparticles by mixing with a microreactor an iron oxide raw material fluid containing at least $Fe^{3+}$ ion, and an iron oxide precipitation fluid containing at least a basic substance.

Step (b) is a step of dispersing the above precipitated iron oxide microparticles in a dispersion medium to obtain iron oxide microparticle dispersion.

The iron oxide raw material fluid is a fluid in which an iron oxide raw material is dissolved or molecularly dispersed in a solvent. The iron oxide raw material is not particularly restricted, but includes an iron compound such as an elementary iron, an iron salt and the like. An iron compound includes an inorganic iron salt such as iron sulfate, iron nitrate, iron chloride and the like, and an organic iron compound such as iron acetate, iron citrate and the like. More specifically, for example, examples of a substance which generates a divalent iron ion, $Fe^{2+}$ ion in a solution, are an inorganic iron (II) salt such as iron (II) sulfate ($FeSO_4$), iron (II) nitrate ($Fe(NO_3)_2$), iron (II) chloride ($FeCl_2$) and the like, an organic iron (II) salt such as iron (II) acetate ($Fe(CH_3COO)_2$), iron (II) citrate ($Fe(C_6H_5O_7M_2)$: M is an alkali metal or ammonium, etc.) and the like, and the like. Examples of a substance which generates a trivalent iron ion, $Fe^{3+}$ ion in a solution, are an inorganic iron (III) salt such as iron (III) sulfate ($Fe_2(SO_4)_3$), iron (III) nitrate ($Fe(NO_3)_3$), iron (III) chloride ($FeCl_3$) and the like, an organic iron (III) salt such as iron (III) acetate (Fe($CH_3COO)_3$ and $Fe(OH)(CH_3COO)_2$), iron (III) citrate ($C_6H_5FeO_7$) and the like, and the like. A hydrate or solvate of the substance which generates $Fe^{3+}$ ion in a solution may be also used. The substance may be used alone, or a plurality of the substances may be mixed and used. Iron oxide in the present invention is preferably α-hematite ($Fe_2O_3$), thus, an iron ion contained in the iron oxide raw material is preferably $Fe^{3+}$. Therefore, it is preferable to use as the iron oxide raw material, a substance that generates $Fe^{3+}$ ion in solution. However, the iron oxide raw material may be prepared by a means such as dissolving a substance which generates $Fe^{2+}$ ion in a solvent, followed by changing $Fe^{2+}$ ion to $Fe^{3+}$ ion with an oxidizing acid such as nitric acid and the like.

A basic substance used for the iron oxide precipitation fluid which is mixed with the iron oxide raw material fluid to precipitate iron oxide, a metal hydroxide such as sodium hydroxide, potassium hydroxide and the like, a metal alkoxide such as sodium methoxide, sodium isopropoxide and the like, further an amine compound such as ammonia, triethylamine, diethylaminoethanol, diethylamine and the like, and the like.

The iron oxide raw material fluid is preferably prepared by dissolving or molecularly dispersing an iron oxide raw material in a solvent. The iron oxide precipitation fluid is preferably prepared by mixing, dissolving or molecularly dispersing a basic substance in a solvent. A solvent used in the iron oxide raw material fluid or the iron oxide precipitation fluid includes, for example, water or an organic solvent, or a mixed solvent consisting of a plurality of these solvents. Water includes tap water, ion-exchanged water, pure water, ultrapure water, RO water and the like. An organic solvent includes an alcohol compound solvent, an amide compound solvent, a ketone compound solvent, an ether compound solvent, an aromatic compound solvent, carbon disulfide, an aliphatic compound solvent, a nitrile compound solvent, a sulfoxide compound solvent, a halogen compound solvent, an ester compound solvent, an ionic liquid, a carboxylic acid compound, and a sulfonic acid compound, and the like. The solvent may be used alone or in combination of two or more thereof.

For preparation of the iron oxide raw material fluid or the iron oxide precipitation fluid in the present invention, it is desirable to use a machine to achieve homogeneous mixing by adding a shearing force or the like to the fluid, for example, a machine to rotate a stirrer of various shapes including rod-like, plate-like and propeller-like shapes in a vessel, a machine equipped with a screen which rotates relative to a stirrer, or the like. As a preferable example of a rotary dispersing machine, the stirring machine disclosed in JP 5147091 can be applied.

Further, the rotary dispersing machine may be a batch type machine or a continuous type machine. When carried out in continuous mode, the continuous type machine may be a machine in which fluids are continuously supplied to and discharged from a stirring tank, or a machine using a continuous mixer without using a stirring tank, or a machine controlling mixing energy appropriately using a known stirrer or stirring means. The stirring energy is explained in detail in JP H04-114725 filed by the present applicant. Stirring methods in the present invention are not particularly limited, and various stirring machines such as a shearing type machine, a friction type machine, a high pressure jet type machine, an ultrasonic machine, and a dissolver, an emulsifier, a dispersing machine, a homogenizer and the like can be used in the present invention. Examples of the rotary dispersing machine include continuous emulsification machines such as Ultra-Turrax (IKA Works, Inc.), Polytron (Kinematica AG), TK Homomixer (Primix Corporation), Ebara Milder (Ebara Corporation), TK Homomic Line Flow (Primix Corporation), Colloid Mill (Shinko-Pantech Co., Ltd.), Thrasher (Nippon Coke & Engineering Co., Ltd.), Trigonal Wet Type Micropulverizer (Mitsui Miike Machinery Co., Ltd.), Cavitron (Eurotech, Ltd.), Fineflow Mill (Pacific Machinery & Engineering Co., Ltd.) and the like; and batch type or dual type emulsification machines such as CLEARMIX (M technique Co., Ltd.), CLEARMIX Dissolver (M technique Co., Ltd.), Filmix (Primix Corporation) and the like. Further, stirring treatment is preferably performed by using a stirring machine equipped with a rotating stirring blade, especially above mentioned CLEARMIX (M Technique Co., Ltd.) and CLEARMIX Dissolver (M Technique Co., Ltd.).

Step (a)

In the present invention, it is preferable to carry out mixing of the iron oxide raw material fluid and the iron oxide precipitation fluid by using a microreactor. Among them, it is preferable to use a machine as shown in FIG. 1, similar to the machine described in Patent Literature 4 and Patent Literature 5. Details of a microreactor is explained below. R represents the rotational direction in FIG. 1 and FIG. 2.

A microreactor (hereinafter, referred to as a fluid processing machine) in this embodiment, is equipped with the first and second opposing processing units 10 and 20, and the first processing unit 10 rotates. Opposing surfaces of both the processing units 10 and 20 are the processing surfaces. The first processing unit 10 possesses the first processing surface 1, and the second processing unit 20 possesses the second processing surface 2.

Both processing surfaces 1 and 2 are connected with the flow paths d1 and d2 of the fluids to be processed, and constitute a part of the flow paths of the fluids to be processed. The interval between both processing surfaces 1 and 2 is adjusted usually to a small interval of 1 mm or less, for example from 0.1 μm to about 50 μm. Thus, the fluids to be processed passing between both processing surfaces 1 and 2 are forced by both processing surfaces 1 and 2 to be a forced thin film fluid.

Then, this fluid processing machine performs fluid processing for precipitating iron oxide microparticles by reacting the first and second fluids to be processed between the processing surfaces 1 and 2.

More specifically, the above machine is equipped with the first holder 11 for holding the first processing unit 10 described above, the second holder 21 for holding the second processing unit 20, a surface approaching pressuring mechanism 43, a rotation drive mechanism (not shown in drawing), the first introduction part d1, the second introduction part d2, and a fluid pressuring mechanisms p1 and p2. As the fluid pressuring mechanisms p1 and p2, a compressor or other pumps may be used.

In the above embodiment, the first processing unit 10 and the second processing unit 20 are ring shaped disks. As a material of the first and second processing units 10 and 20, metal, carbon, ceramic, sintered metal, abrasion resistant steel, sapphire, hardened metal, and hard material treated with lining, coating, plating or the like may be used. In the above embodiment, the first and second opposing processing surfaces 1 and 2 in the first and second processing units 10 and 20 are mirror polished, and the arithmetic mean roughness is 0.01 to 1.0 μm.

In the above embodiment, the second holder 21 is fixed to the machine, and the first holder 11 rotates which is attached to a rotating shaft 50 of the rotation drive mechanism similarly fixed to the machine, and the first processing unit 10 supported on the first holder 11 rotates relative to the second processing unit 20. Of course, the second processing unit 20 may rotate instead, or both may rotate.

Further, in the present invention, the rotational speed may be, for example, 350 to 5000 rpm.

In the above embodiment, the second processing unit 20 approaches to and separates from the first processing unit 10 in the direction of the rotation shaft 50, and the part opposite to the processing surface 2 side of the second processing unit 20 is retractably housed in the housing portion 41 provided in the second holder 21. However, on the contrary, the first processing unit 10 may approach to and separate from the second processing unit 20, or both processing units 10 and 20 may approach to and separate from each other.

The housing portion 41 is a concavity housing the part opposite to the processing surface 2 side of the second processing unit 20, and is a groove formed in a ring shape. The housing portion 41 houses the second processing unit 20, with sufficient clearance that the part opposite to the processing surface 2 side of the second processing unit 20 can appear and disappear.

The surface approaching pressuring mechanism is a mechanism for generating a pushing force in the direction of approximating the first processing surface 1 of the first processing unit 10 and the second processing surface 2 of the second processing unit 20 (hereinafter, referred to as surface approaching pressure). By a balance between this surface approaching pressure and the force of separating both processing surfaces 1 and 2 by the fluid pressure, the interval between both processing surfaces 1 and 2 is maintained minute, to generate a thin film fluid with a minute film thickness of nm unit to µm unit. In the above embodiment, the surface approaching pressuring mechanism gives a surface approaching pressure with a spring 43 provided in the second holder 21 by energizing the second processing unit 20 toward the first processing unit 10.

The first fluid to be processed pressurized by the surface approaching pressuring mechanism p1 is introduced into the space between the processing units 10 and 20 from the first introduction part d1.

On the other hand, the second fluid to be processed pressurized by the surface approaching pressuring mechanism p2 is introduced into the space between the processing units 10 and 20 from the opening d20 formed on the second processing surface through a passage provided from the second introduction part d2 into the interior of the second processing unit 20.

In the opening d20, the first fluid to be processed and the second fluid to be processed are merged and mixed.

At that time, the mixed fluids to be processed become a thin film fluid forced by the processing surfaces 1 and 2 to maintain the above minute interval, and are forced to move outside of the ring shape of both processing surfaces 1 and 2. Since the first processing unit 10 rotates, the mixed fluids to be processed do not move linearly from the inside of the ring shape of both processing surfaces 1 and 2 to the outside, but move in a substantially spiral shape from the inside to the outside by the combination vector of the mobile vector in the radial direction and the mobile vector in the circumferential direction acting on the fluid to be processed.

Figure 2:
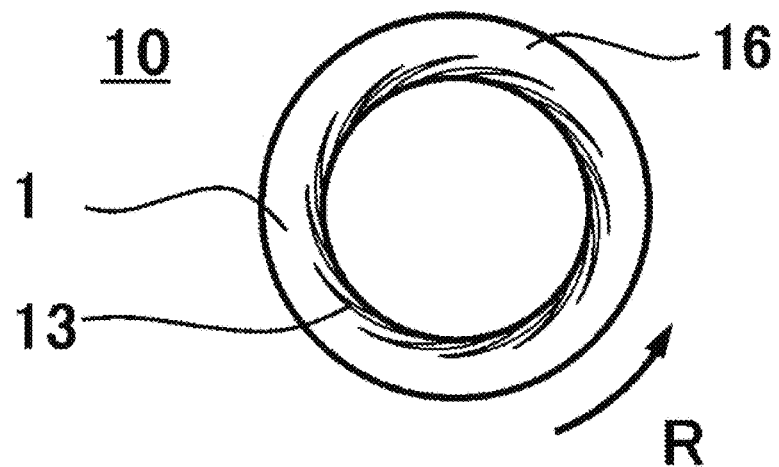
FIG. 2 shows a main part enlarged view of the processing surface of the fluid processing machine of FIG. 1.

Here, as shown in FIG. 2, a groove like concavity 13 may be formed on the first processing surface 1 of the first processing unit 10, which extends from the center side of the first processing unit 10 to the outside, or in the radial direction. The planar shape of the concavity 13 may be one extending curvingly or spirally on the first processing surface 1, and although not shown, one extending straight outward, one bending or curving in an L shape or the like, continuous one, intermittent one, one having branches. Further, the concavity 13 formed on the second processing surface 2 may be performed, and also the concavity 13 formed on both the first and second processing surfaces 1 and 2 may be performed. Formation of such concavity 13 may give a micropump effect, and also an effect to transfer the fluids to be treated between the first and second processing surfaces 1 and 2.

The base end of the concavity 13 desirably reaches the inner periphery of the first processing unit 10. The tip end of the concavity 13 extends towards the outer peripheral surface of the first processing surface 1, and the depth gradually decreases from the base end to the tip end. A flat surface 16 without concavity 13 is provided between the tip end of the concavity 13 and the outer peripheral surface of the first processing surface 1.

The above opening d20 is preferably provided at a position facing the flat surface of the first processing surface 1. In particular, the opening d20 is preferably provided at a position facing the flat surface 16, which is a downstream side from the position where the flow direction of the fluids to be processed as introduced is converted into the flow direction of the spiral laminar flow formed between both processing surfaces by the micropump effect. Thereby, it is possible to mix a plurality of fluids to be processed at a laminar flow condition, and to precipitate microparticles.

It is preferred to provide directionality to the second introduction part d2. For example, the introduction direction from the opening d20 of the second processing surface 2 may be inclined at a predetermined elevation angle relative to the second processing surface 2. The introduction direction from the opening d20 of the second processing surface 2 may have directionality on the plane along the above second processing surface 2, and the introduction direction of the second fluid to be processed may be the radially outward direction from the center in the radial direction component, and the forward direction in the rotation direction component of the fluids between the rotating processing surfaces. Thus, the flow of the first fluid to be processed at the opening d20 is a laminar flow, and the second introduction part d2 has directionality, and thereby the second fluid to be processed can be introduced between the processing surfaces 1 and 2 while suppressing occurrence of turbulence against the first fluid to be processed.

The fluid discharged outside both processing units 10 and 20 is collected in the beaker b as a discharged liquid through the vessel v. In the embodiment of the present invention, the discharged fluid includes iron oxide microparticles as described below.

Types of the above fluids to be processed and number of the flow paths are two in the example of FIG. 1, but may be three or more. Shape, size and number of the openings for the introduction provided in respective processing units, may be changed and carried out appropriately without any particular restriction. For example, as shown in FIG. 1, shape of the opening d20 may be a concentric circular ring shape surrounding the central opening of the processing surface 2 which is a ring shape disc, and the ring shape opening may be continuous or discontinuous. The introduction opening may be provided just ahead of or at further upstream side of the space between the above first and second processing surfaces 1 and 2.

In case of producing the iron oxide microparticles using the above fluid processing machine, an iron oxide raw material fluid is introduced from the first introduction part d1 as the first fluid to be processed, and an iron oxide precipitation fluid is introduced from the second introduction part, and the above at least two kinds of fluids are mixed between the processing surfaces 1 and 2, and thereby the iron oxide microparticles can be to precipitated. In the present invention, it is preferable that liquid sending temperature of the iron oxide raw material fluid is the boiling point or higher. Thereby, there is an advantage that the obtained iron oxide microparticles tend to have high crystallinity.

In the present invention, the second fluid to be processed may be introduced from the first introduction part d1, and the first fluid to be processed may be introduced from the second introduction part d2, as long as the above mentioned processing can be performed between the processing surfaces 1 and 2. For example, the expressions first and second regarding fluids, only have implications for identification as the fluid is the n th fluid among a plurality of fluids present, and the third or later fluids may be present as described above.

In the present invention, a primary particle size of the precipitated iron oxide microparticles is preferably 25 nm or less. When particles of a primary particle size of 25 nm or less are dispersed as shown in the following step (b), an ultraviolet protective agent composition wherein the haze value is 2.0% or less, and the transmittance of the light of the wavelengths of 200 to 420 nm is 2.0% or less, can be produced.

Step (a-2)

In the present invention, it is preferable to include step (a-2) of performing an additional stirring treatment to the discharged fluid to be processed, after discharging the fluid to be processed from the space between the processing surfaces and before step (b). In case of performing the additional stirring treatment, various dispersants or surfactants described below may be added to the discharged fluid to be processed.

A machine for the stirring treatment is overlapped with the above mentioned machines used for preparation of the iron oxide raw material fluid or the iron oxide precipitation fluid in the present invention, but it is desirable to use a machine to achieve homogeneous mixing by adding a shearing force or the like to the fluid, for example, a machine to rotate a stirrer of various shapes including rod-like, plate-like and propeller-like shapes in a vessel, a machine having a screen which rotates relative to a stirrer, or the like. As a preferable example of a rotary dispersing machine, the stirring machine disclosed in JP 5147091 can be applied.

Further, the rotary dispersing machine may be a batch type machine or a continuous type machine. When carried out in continuous mode, the continuous type machine may be a machine in which fluids are continuously supplied to and discharged from a stirring tank, or a machine using a continuous mixer without using a stirring tank, or a machine controlling mixing energy appropriately using a known stirrer or stirring means. The stirring energy is explained in detail in JP H04-114725 filed by the present applicant. Stirring methods in the present invention are not particularly limited, and various stirring machines such as a shearing type machine, a friction type machine, a high pressure jet type machine, an ultrasonic machine, and a dissolver, an emulsifier, a dispersing machine, a homogenizer and the like can be used in the present invention. Examples of the rotary dispersing machine include continuous emulsification machines such as Ultra-Turrax (IKA Works, Inc.), Polytron (Kinematica AG), TK Homomixer (Primix Corporation), Ebara Milder (Ebara Corporation), TK Homomic Line Flow (Primix Corporation), Colloid Mill (Shinko-Pantech Co., Ltd.), Thrasher (Nippon Coke & Engineering Co., Ltd.), Trigonal Wet Type Micropulverizer" (Mitsui Miike Machinery Co., Ltd.), Cavitron (Eurotech, Ltd.), Fineflow Mill (Pacific Machinery & Engineering Co., Ltd.) and the like; and batch type or dual type emulsification machines such as CLEARMIX (M technique Co., Ltd.), CLEARMIX Dissolver (M technique Co., Ltd.), Filmix (Primix Corporation) and the like. Further, stirring treatment is preferably performed by using a stirring machine equipped with a rotating stirring blade, especially above mentioned CLEARMIX (M Technique Co., Ltd.) and CLEARMIX Dissolver (M Technique Co., Ltd.).

By performing the stirring treatment, transmittance of the iron oxide microparticle dispersion for the wavelength of 420 nm is lowered as compared with the case without stirring treatment. Also, in case a dispersants which is described below is added to the discharged fluid to be processed when performing stirring treatment, transmittance of the iron oxide microparticle dispersion for the wavelength of 420 nm is lowered as compared with the case without stirring treatment. Thus, by performing stirring treatment, the iron oxide microparticle dispersion absorbs or shields ultraviolet rays more as compared with the case without stirring treatment, and the protective ability against ultraviolet rays can be improved.

The present inventors found that both a primary particle diameter and crystallinity can be controlled by performing this stirring treatment appropriately. The present inventors found that a primary particle size and crystallinity affect dispersibility (secondary particle diameter), haze value, transmittance and molar absorption coefficient, and a high performance ultraviolet protective agent composition and a method of producing the same have been completed. For example, it has been found that stirring treatment can improve crystallinity, even if the primary particle diameter is substantially the same, so that the absorption region may extend from ultraviolet region to visible region.

Step (b)

The present invention comprises step (b) of dispersing the precipitated iron oxide microparticles in a solvent which can be a dispersion medium to obtain iron oxide microparticle dispersion. The solvent which can be a dispersion medium is not particularly limited, but include, for example, water or an organic solvent, or a mixed solvent consisting of a plurality of these solvents. Water includes tap water, ion-exchanged water, pure water, ultrapure water, RO water and the like. An organic solvent includes an alcohol compound solvent, an amide compound solvent, a ketone compound solvent, an ether compound solvent, an aromatic compound solvent, carbon disulfide, an aliphatic compound solvent, a nitrile compound solvent, a sulfoxide compound solvent, a halogen compound solvent, an ester compound solvent, an ionic liquid, a carboxylic acid compound, and a sulfonic acid compound, and the like. The solvent may be used alone or in combination of two or more thereof. In the present invention, it is preferable to disperse the iron oxide microparticles in the dispersion medium until the secondary particle diameter, that is dispersion diameter, becomes 50 nm or less.

A dispersing machine using for dispersing is overlapped with the above mentioned machines used for preparation of the iron oxide raw material fluid or the iron oxide precipitation fluid in the present invention, but it is desirable to use a machine to achieve homogeneous mixing by adding a shearing force or the like to the fluid, for example, a machine to rotate a stirrer of various shapes including rod-like, plate-like and propeller-like shapes in a vessel, a machine having a screen which rotates relative to a stirrer, or the like. As a preferable example of a rotary dispersing machine, the stirring machine disclosed in JP 5147091 can be applied.

Further, the rotary dispersing machine may be a batch type machine or a continuous type machine. When carried out in continuous mode, the continuous type machine may be a machine in which fluids are continuously supplied to and discharged from a stirring tank, or a machine using a continuous mixer without using a stirring tank, or a machine controlling mixing energy appropriately using a known stirrer or stirring means. The stirring energy is explained in detail in JP H04-114725 filed by the present applicant. Stirring methods in the present invention are not particularly limited, and various stirring machines such as a shearing type machine, a friction type machine, a high pressure jet type machine, an ultrasonic machine, and a dissolver, an emulsifier, a dispersing machine, a homogenizer and the like can be used in the present invention. Examples of the rotary dispersing machine include continuous emulsification machines such as Ultra-Turrax (IKA Works, Inc.), Polytron (Kinematica AG), TK Homomixer (Primix Corporation), Ebara Milder (Ebara Corporation), TK Homomic Line Flow (Primix Corporation), Colloid Mill (Shinko-Pantech Co., Ltd.), Thrasher (Nippon Coke & Engineering Co., Ltd.), Trigonal Wet Type Micropulverizer" (Mitsui Miike Machinery Co., Ltd.), Cavitron (Eurotech, Ltd.), Fineflow Mill (Pacific Machinery & Engineering Co., Ltd.) and the like; and batch type or dual type emulsification machines such as CLEARMIX (M technique Co., Ltd.), CLEARMIX Dissolver (M technique Co., Ltd.), Filmix (Primix Corporation) and the like. Further, stirring treatment is preferably performed by using a stirring machine equipped with a rotating stirring blade, especially above mentioned CLEARMIX (M Technique Co., Ltd.) and CLEARMIX Dissolver (M Technique Co., Ltd.).

In the present invention, various dispersants or surfactants may be used depending on the purpose or necessity. Not particularly limited, as a surfactant or dispersant, various generally used commercially available products, a finished product, a newly synthesized product and the like may be used. The examples are an anionic surfactant, a cationic surfactant, a nonionic surfactant, a dispersant such as various polymers and the like. These may be used alone or in combination of two or more thereof. The surfactant or dispersant may be included in either or both of the iron oxide raw material fluid and the iron oxide precipitation solvent. In addition, the surfactant or dispersant may be included in the third fluid different from the iron oxide raw material fluid and the iron oxide precipitation solvent which is explained later. In addition, it may be included in the dispersion medium.

In the present invention, the iron oxide microparticle dispersion is not limited to a dispersion obtained by dispersing in a liquid dispersion medium. A dispersion dispersed in a solid such as a glass or resin may be also carried out.

In the present invention, by including step (a) and step (b), an ultraviolet protective agent composition wherein a haze value of the iron oxide microparticle dispersion is 2.0% or less, and a transmittance for the light of the wavelengths of 200 to 420 nm is 2.0% or less, can be obtained. The present inventors consider that the present invention was led by the fact that a molar absorption coefficient for the light of the wavelengths of 200 to 420 nm of the iron oxide microparticles in the iron oxide microparticle dispersion prepared by the method including step (a) and step (b) using the microreactor, is higher than that of conventional one. In the present invention, it is preferable that a molar absorption coefficient of the iron oxide microparticles for the light of the wavelength of 400 nm is 500 L/(mol·cm) or more, and a molar absorption coefficient for the light of the wavelength of 220 nm is 3000 L/(mol·cm) or more. A molar absorption coefficient can be calculated from the absorbance and the molar concentration in ultraviolet-visible absorption spectrum measurement, by the following formula.

$$\varepsilon = A/(c \cdot l)$$

In the formula, $\varepsilon$ is a material specific constant, and is referred to as a molar absorption coefficient. Since it means a reciprocal number of the light intensity when a light passes through a liquid at 1 mol/L with a thickness of 1 cm, the unit is L/(mol·cm). A is an absorbance in ultraviolet-visible absorption spectrum measurement. c is a molar concentration of a sample (mol/L). l is a length through which a light is transmitted (optical path length), typically a thickness of a cell in measuring the ultraviolet-visible absorption spectrum.

Haze value is a numerical value indicating transparency. When an ultraviolet protective agent composition having a haze value exceeding 2% is applied, for example, on a paint for a building or car, a paint color as a foundation is impaired, and thus the intended coloration is inhibited. Also when an ultraviolet protective agent composition having a haze value exceeding 2% and a low transmittance is applied to human skin or the like, the texture and appearance are impaired, which is not preferable.

This point is also the effect exhibited when an ultraviolet protective agent composition is actually used, which is caused by that a primary particle diameter and a secondary particle diameter of the iron oxide used for the ultraviolet protective agent composition of the present invention is smaller than those of the conventional iron oxide, and the molar absorption coefficient is higher than that of the conventional iron oxide, and thus it is not necessary to use a large amount of iron oxide.

Molar absorption coefficient is an ultraviolet absorbing ability of iron oxide per unit mole. Performance as an ultraviolet protective composition is properly exerted, and a large amount required is reduced when used in a method such as coating, and possibility of damaging haze value and transmittance can be reduced, which are caused by that a molar absorption coefficient of the iron oxide particle dispersion for the light of the wavelength of 400 nm is 500 L/(mol·cm) or more, and a molar absorption coefficient of the same for the light of the wavelength of 220 nm is 3000 L/(mol·cm) or more.

The Iron oxide microparticles in the iron oxide microparticles dispersion prepared in the present invention, has smaller primary particle diameter and secondary particle diameter than those of a conventional iron oxide, and has larger surface area and high crystallinity, which are considered to be factors of high molar absorption coefficient mentioned above. Shape of the particles has lower influence than those of the factors above, and may be one of various shapes, but substantially spherical shape is desirable.

It is effective for obtaining particles which have smaller primary and secondary particle diameters than those of a conventional particles, high crystallinity and substantially spherical shape, to perform a step of precipitating the above iron oxide microparticles by mixing the above fluids to be processed between two processing surfaces using the above fluid processing machine as step (a) by applying the technology described in Patent Literatures 4 and 5.

Patent Literatures 4 and 5 describe that control of a particle diameter, monodispersity, and also crystallinity and degree of crystallization of the obtained magnetic microparticles, can be adjusted by varying rotational speed of the processing surfaces and distance between the processing surfaces, and flow rate and temperature of the thin film fluid, or material concentration. However, Patent Literatures 4 and 5 do not describe sufficient information regarding improving crystallinity of the iron oxide particles and more preferably obtaining single crystals of the iron oxide particles. The present inventors proceeded study on the basis of the technique disclosed in Patent Literatures 4 and 5, but could not obtain single crystals of iron oxide particles simply by controlling temperature of the thin film fluid under a relatively low pressure condition. Then, as a result of intensive studies by the inventors after trials and errors, the inventors have found that it is possible to improve crystallinity of iron oxide particles drastically by raising temperature of the iron oxide raw material fluid to a predetermined temperature or higher under a relatively high pressure condition.

Specifically, it was found that crystallinity of the iron oxide particles can be dramatically improved, by making the introduction pressure of both the fluids to be processed of the iron oxide raw material fluid and the iron oxide precipitation fluid in the space between the processing surfaces exceed the standard pressure, and by making the temperature of the iron oxide raw material fluid to be introduced between the processing surfaces be higher than the normal boiling point of the iron oxide raw material fluid, and be lower than the boiling point under the introduction pressure. According to this method, iron oxide particles more than 90% of which are single crystals can be obtained, and also iron oxide particles having a haze value of 2.0% or less and a transmittance of 2.0% or less for the light of the wavelengths of 200 to 420 nm can be produced.

The normal boiling point of the iron oxide raw material fluid may vary depending on type and blending ratio of the iron oxide raw material fluid, but in practice, the normal boiling point of the iron oxide raw material fluid is calculated, and temperature of the iron oxide raw material fluid to be supplied may be set to a higher temperature than the calculated temperature.

pH of the fluid mixed in the space between the processing surfaces in step (a), or pH of the fluid obtained in step (a-2) is preferably 6 to 14, more preferably 8 to 12. In particular, when pH of the fluid is 8 or more, 90% or more of the iron oxide microparticles may be single crystals.

Further, reaction heat such as neutralization heat is sometimes generated by mixing the iron oxide raw material fluid and the iron oxide precipitation fluid. The thermal energy of the fluid to be processed accompanied by the heat generated by the reaction heat such as neutralization heat may affect precipitation and crystal growth of iron oxide microparticles, to obtain single crystals of iron oxide microparticles.

As a method of evaluating whether the iron oxide microparticles are single crystals, it can be evaluated by a method of observing directly by TEM observation, or by a method of calculating the ratio d/D between the particle diameter (D) obtained in an electron microscope observation with a transmission electron microscope (TEM) or a scanning electron microscope (SEM) and the crystal lattice (d) measured by an X-ray diffraction measurement (XRD measurement). In the electron microscopic observation, criteria of deciding whether or not the individual particles are single crystals, is to determine as single crystals when lattice strips (atomic arrangement in a crystal) are observed in one direction, and to determine as not single crystals when lattice stripes are disordered or when crystal boundary is observed.

EXAMPLE

Hereinafter, the present invention is explained in detail with reference to Examples and the like which show the structures and effects of the present invention. The present invention is not limited to the following examples.

Example 1

An iron oxide raw material fluid is used as Liquid A, and an iron oxide precipitation fluid is used as Liquid B. Liquid A and Liquid B is mixed with a microreactor to precipitate iron oxide microparticles. The obtained iron oxide microparticles are dispersed with a dispersion fluid.

The microreactor (product name: ULREA, M Technique Co., Ltd.) was used. In this example, Liquid A corresponded to the first fluid to be processed introduced from the first introduction part d1 of the microreactor shown in FIG. 1, and Liquid B corresponded to the second fluid to be processed introduced from the second introduction part d2 likewise. The first introduction part d1 and the second introduction part d2 may be replaced arbitrarily. Analysis of the obtained iron oxide microparticles was carried out under the following conditions.

For the X-ray diffraction (XRD) measurement, the powder X-ray diffractometer (product name: X'PertPRO MPD, PANalytical B.V.) was used. The measurement condition was measurement range of 10 to 100°, Cu anticathode, tube voltage of 45 kV, tube current of 40 mA, and scanning speed of 16°/min. The crystallite diameters were calculated using the peaks near 44° with polycrystalline silicon plate as a reference.

For TEM observation, the transmission electron microscopy JEM-2100 (JEOL Ltd.) was used. The observation condition was the acceleration voltage of 80 kV, and the observation magnification of 10,000 times or more. The primary particle diameter D1 of the iron oxide microparticles of Examples and Comparative Examples was the average value (average primary particle diameter) of the particle diameters of 100 particles measured by TEM observation.

For evaluation of the secondary particle diameter (volume average particle diameter), was used a particle size distribution analyzer (UPA-UT151, Nikkiso Co., Ltd.). As the measurement condition, the measurement solvent was propylene glycol, and the solvent refractive index was 1.43. The refractive index of the particles was 2.94, and the specific gravity of the particles was 5.24 g/cm$^3$. The measured volume average particle diameter is referred to as D2.

For the ultraviolet-visible transmission absorption spectrum measurement, the ultraviolet-visible absorption spectrophotometer (product name: UV-2450, Shimadzu Corporation) was used. The measurement range was from 200 nm to 800 nm, and the sampling rate was 0.2 nm, and the measurement speed was slow speed. The transmission spectrum was measured at an iron oxide concentration of 0.005 wt %. The absorption spectrum was measured at an iron oxide concentration of 0.005 wt % or less. After the absorption spectrum measurement, the molar absorption coefficient was calculated from the absorbance obtained from the measurement result and the iron oxide concentration of the measurement liquid. Then, graph was prepared showing the measurement wavelength on the horizontal axis and the molar absorption coefficient on the vertical axis. A liquid cell of thickness of 1 mm was used for measurements.

For the haze value measurement, the haze value meter (Model HZ-V3, Suga Test Instruments Co., Ltd.) was used. The optical condition was the double-beam method and D65 light as a light source which corresponds to JIS K 7136 and JIS K 7361. A liquid cell of thickness of 1 mm was used for measurements, and the same liquids as used in the ultraviolet-visible transmission absorption spectrum measurement were measured.

Liquid A was prepared by mixing iron (III) nitrate nonahydrate and pure water at the weight ratio of 2.0/98.0, and stirring them using CLEARMIX (product name: CLM-2.2 S, M Technique Co., Ltd.) at the rotational speed of 20000 rpm at the treatment temperature of 24 to 60° C. for the treatment time of 60 min to be mixed and dissolved. Liquid B was prepared by mixing sodium hydroxide and pure water at the weight ratio of 9.0/91.0, and stirring them using CLEARMIX at the rotational speed of 8000 rpm at the treatment temperature of 50° C. for the treatment time of 30 min to be mixed and dissolved.

Examples 1 to 8

Using the microreactor shown in FIG. 1, Liquid A and Liquid B of the formulation shown in Table 1 were introduced between the processing surfaces 1 and 2 in the processing conditions of Table 1, and were mixed in a thin film fluid formed between the processing surfaces 1 and 2 to precipitate iron oxide microparticles. Slurry containing the iron oxide microparticles precipitated between the processing surfaces 1 and 2 (hereinafter, also referred to as a discharged liquid) was discharged from the space between the processing surfaces 1 and 2, and was collected in the beaker b through the vessel v. The rotational speed of the first processing unit 10 was 1700 rpm.

"Fluid temperature between processing surfaces" in Table 1 was calculated from the following figure.

$$c=(a1 \times a2 + b1 \times b2)/(a2+b2)$$

wherein, a1: temperature of the iron oxide raw material fluid a2: flow rate of the iron oxide raw material fluid per unit time b1: temperature of the iron oxide precipitation fluid b2: flow rate of the iron oxide precipitation fluid per unit time Regarding the abbreviations set forth in Table 1, $Fe(NO_3)_3 \cdot 9H_2O$ is iron (III) nitrate nonahydrate, NaOH is sodium hydroxide, SDS is sodium dodecyl sulfate, and HEC is hydroxy ethyl cellulose.

In Examples 1 and 4 to 8, the discharged liquid collected in the beaker b was allowed to stand until the temperature was 60 □ or less, to precipitate iron oxide microparticles. In Examples 2 and 3, the stirring treatment was performed to the discharged liquid collected in the beaker b, under the conditions shown in Table 1, and the liquid obtained after the stirring treatment was allowed to stand until the temperature was 60 □ or less, to precipitate iron oxide microparticles. As stirring treatment, in Example 2, the discharged liquid collected in the beaker b was stirred for 1 hour at 100° C. without cooling, using CLEARMIX at 20000 rpm. In Example 3, to the discharged liquid collected in the beaker b was added a surfactant SDS in the amount of 100 wt % based on iron oxide, and the mixture was stirred for 1 hour at 100° C. without cooling, using CLEARMIX at 20000 rpm.

(Washing and Collection of Iron Oxide Microparticles)

The supernatant in the beaker b was removed, and 20 to 1,500 times by weight of pure water relative to the weight of the precipitated iron oxide microparticles was added thereto, and the mixture was stirred using CLEARMIX at the rotational speed of 6000 rpm, at the treatment temperature of 25° C. for the treatment time of 5 min to wash the iron oxide microparticles. After three washing treatments above, the iron oxide microparticles were precipitated again, and the supernatant was removed to obtain a water containing wet cake of the iron oxide microparticles.

(Preparation of Iron Oxide Dispersion and Preparation of Various Measurement Samples)

A part of the water containing wet cake of the iron oxide microparticles was added to propylene glycol, and dispersion treatment using CLEARMIX at 20000 rpm for 30 min was performed to obtain an iron oxide microparticle dispersion. Haze value, particle size distribution and ultraviolet-visible transmission absorption spectrum were measured by diluting the obtained dispersion with propylene glycol. Haze value, particle size distribution and ultraviolet-visible transmission spectrum were measured using a dispersion at the iron oxide concentration of 0.005 wt %. Ultraviolet-visible absorption spectrum was measured using a dispersion at the iron oxide concentration of 0.005 wt % or less. Further, the obtained dispersion was diluted with isopropyl alcohol, and dispersion treatment was performed with an ultrasonic cleaner, and the obtained dispersion was dropped on a collodion film and dried to give a TEM observation sample. Further, the water containing wet cake of the iron oxide microparticles obtained after washing was dried at −0.10 MpaG at 20° C. for over 15 hours to obtain iron oxide microparticles. The results are shown in Table 2. In the results shown in Table 2, the transmittance (wavelengths of 650 to 800 nm) was determined as "Pass" in case that the transmittance for the wavelengths of 650 to 800 nm was 80% or more in the result of the ultraviolet-visible transmission spectrum measurement of the iron oxide microparticle dispersion, and the transmittance (wavelengths of 650 to 800 nm) was determined as "Not" in case that the transmittance for the wavelengths of 650 to 800 nm was less than 80%. In addition, in the results shown in Table 2, "pH after treatment" shows the pH of the solution obtained after stirring treatment in the Examples and Comparative Examples in which stirring treatment was performed, and "pH after treatment" shows pH of the discharged liquid collected in the beaker b in the Examples and Comparative Examples in which stirring treatment was not performed. Incidentally, as shown in Table 2, all samples obtained in Comparative Examples described below did not satisfy the conditions "a haze value of an iron oxide microparticle dispersion is 2.0% or less, and a transmittance of an iron oxide microparticle dispersion for the light of the wavelengths of 200 to 420 nm is 2.0% or less", and thus, are considered unsuitable for an ultraviolet protective agent composition.

Comparative Example 1

As Comparative Example 1, iron (III) oxide ($\alpha$-$Fe_2O_3$) produced by Wako Pure Chemical Industry Ltd., was dispersed in propylene glycol in the same manner as in Example 1, and haze value, particle size distribution and ultraviolet-visible transmission absorption spectrum were measured. Haze value, particle size distribution and ultraviolet-visible transmission spectrum were measured using a dispersion at the iron oxide concentration of 0.005 wt %. Ultraviolet-visible absorption spectrum was measured using a dispersion at the iron oxide concentration of 0.005 wt % or less. Further, the obtained dispersion was diluted with isopropyl alcohol, and dispersion treatment was performed with an ultrasonic cleaner, and the obtained dispersion was dropped on a collodion film and dried to give a TEM observation sample.

Comparative Examples 2 to 10

Iron oxide microparticles were precipitated in the same manner as in Examples 1 to 8, except for the formulations of the iron oxide raw material fluid and the iron oxide precipitation fluid and the treatment conditions in Table 1. Slurry containing the iron oxide microparticles precipitated between the processing surfaces 1 and 2 (hereinafter, also referred to as a discharged liquid) was discharged from the space between the processing surfaces 1 and 2, and was collected in the beaker b through the vessel v.

In Comparative Examples 4 and 7 to 10, the discharge liquid collected in the beaker b was allowed to stand until the temperature was 60 □ or less, to precipitate iron oxide microparticles. In Comparative Examples 2, 3, 5 and 6, the stirring treatment was performed to the discharged liquid collected in the beaker b, under the conditions shown in Table 1, and the liquid obtained after the stirring treatment was allowed to stand until the temperature was 60 □ or less, to precipitate iron oxide microparticles. As a stirring treatment, in Comparative Example 2, to the discharged liquid collected in the beaker b was added a polymer activator, hydroxyethyl cellulose (hereinafter, referred to as HEC) in the amount of 100 wt % based on iron oxide without cooling, and the mixture was stirred for 1 hour at 100° C., using CLEARMIX at 20000 rpm. In Comparative Example 3, to the discharged liquid collected in the beaker b was added a basic solvent, sodium hydroxide (hereinafter, also referred to as NaOH) in the amount of 1.2 wt % based on iron oxide without cooling, and the mixture was stirred for 1 hour at 100° C., using CLEARMIX at 20000 rpm. Further, in Comparative Example 5, the discharge liquid collected in the beaker b was stirred for 1 hour at 100° C. without cooling, using CLEARMIX at 20000 rpm. In Comparative Example 6, to the discharged liquid collected in the beaker b was added sodium dodecyl sulfate in the amount of 100 wt % based on iron oxide, and the mixture was stirred for 1 hour at 100° C. without cooling, using CLEARMIX at 20000 rpm.

Figure 25:
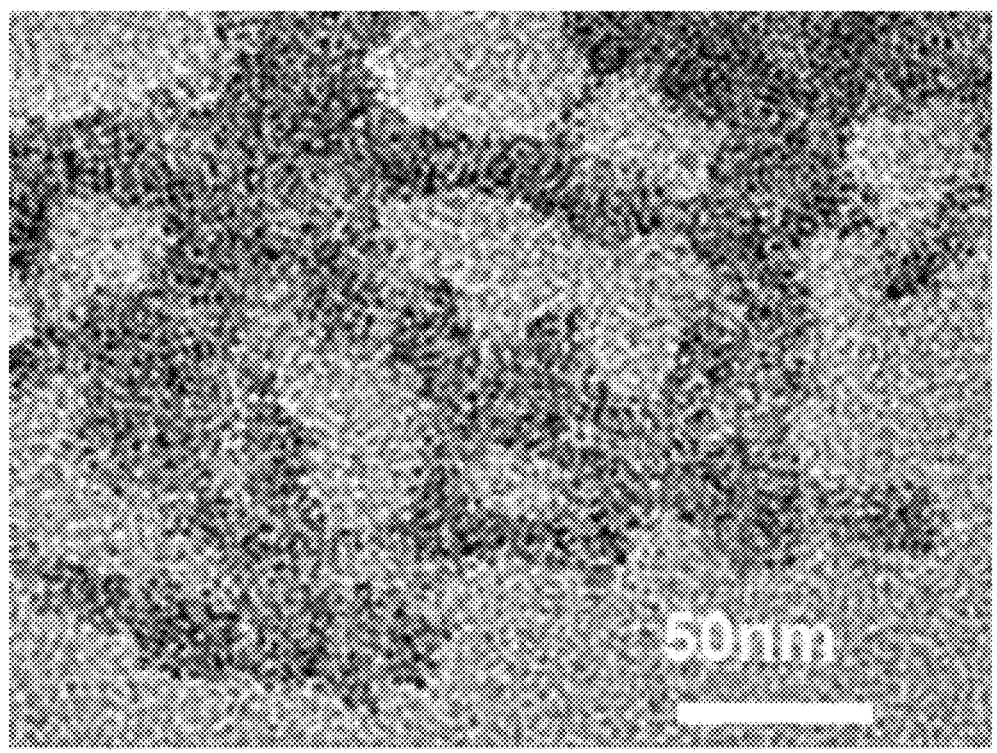
FIG. 25 shows a TEM photograph of the iron oxide microparticles obtained in Comparative Example 9.

Washing and collection of iron oxide microparticles, preparation of iron oxide microparticle dispersion, and preparation of various measurement samples were conducted in the same manner as in Examples 1 to 8. The results are shown in Table 2. In Comparative Examples 9 and 10, crystallinity was low to the extent that its primary particle diameter could not be determined by TEM observation so that single crystal ratio could not be calculated. FIG. 25 shows a TEM photograph of the iron oxide microparticles obtained in Comparative Example 9.

TABLE 1

| | | Formulation of iron oxide raw material fluid (Liquid A) | | | | Formulation of iron oxide precipitation solvent (Liquid B) | | | | Introduction flow rate | |
|---|---|---|---|---|---|---|---|---|---|---|---|
| | | Solvent/ formulation [wt %] | $Fe^{3+}$/ formulation [wt %] | pH | pH measure temp. [° C.] | Basic solvent/ formulation [wt %] | Solvent/ formulation [wt %] | pH | Liquid A [ml/min] | Liquid B [ml/min] |
| Example | 1 | Pure water | 98.00 Fe(NO$_3$)$_3$9H$_2$O | 2.00 | 1.90 | 34.1 | NaOH | 9.00 | Pure water | 91.00 | >14 | 420 | 30 |
| | 2 | | | | | | | | | | | |
| | 3 | | | | | | | | | | | |
| | 4 | Pure water | 96.00 Fe(NO$_3$)$_3$9H$_2$O | 4.00 | 1.42 | 34.1 | NaOH | 18.00 | Pure water | 82.00 | >14 | 420 | 29 |
| | 5 | Pure water | 96.00 Fe(NO$_3$)$_3$9H$_2$O | 4.00 | 1.42 | 34.1 | NaOH | 18.00 | Pure water | 82.00 | >14 | 420 | 30 |
| | 6 | Pure water | 96.00 Fe(NO$_3$)$_3$9H$_2$O | 4.00 | 1.42 | 34.1 | NaOH | 18.00 | Pure water | 82.00 | >14 | 420 | 31 |
| | 7 | Pure water | 96.00 Fe(NO$_3$)$_3$9H$_2$O | 4.00 | 1.42 | 34.1 | NaOH | 18.00 | Pure water | 82.00 | >14 | 420 | 32 |
| | 8 | Pure water | 96.00 Fe(NO$_3$)$_3$9H$_2$O | 4.00 | 1.42 | 34.1 | NaOH | 18.00 | Pure water | 82.00 | >14 | 420 | 33 |
| Comparative Example | 1 | Reagent α-ferric oxide (Kanto Chemical Co., Inc.) | | | | | | | | | | |
| | 2 | Pure water | 98.00 Fe(NO$_3$)$_3$9H$_2$O | 2.00 | 1.90 | 34.1 | NaOH | 9.00 | Pure water | 91.00 | >14 | 420 | 30 |
| | 3 | Pure water | 98.00 Fe(NO$_3$)$_3$9H$_2$O | 2.00 | 1.90 | 34.1 | NaOH | 9.00 | Pure water | 91.00 | >14 | 420 | 30 |
| | 4 | Pure water | 98.00 Fe(NO$_3$)$_3$9H$_2$O | 2.00 | 1.90 | 34.1 | NaOH | 9.00 | Pure water | 91.00 | >14 | 420 | 30 |
| | 5 | | | | | | | | | | | |
| | 6 | | | | | | | | | | | |
| | 7 | Pure water | 96.00 Fe(NO$_3$)$_3$9H$_2$O | 4.00 | 1.42 | 34.1 | NaOH | 18.00 | Pure water | 82.00 | >14 | 420 | 25 |
| | 8 | Pure water | 96.00 Fe(NO$_3$)$_3$9H$_2$O | 4.00 | 1.42 | 34.1 | NaOH | 18.00 | Pure water | 82.00 | >14 | 420 | 35 |
| | 9 | Pure water | 96.00 Fe(NO$_3$)$_3$9H$_2$O | 4.00 | 1.42 | 34.1 | NaOH | 18.00 | Pure water | 82.00 | >14 | 420 | 30 |
| | 10 | Pure water | 96.00 Fe(NO$_3$)$_3$9H$_2$O | 4.00 | 1.42 | 34.1 | NaOH | 18.00 | Pure water | 82.00 | >14 | 420 | 30 |

TABLE 1-continued

| | | Introduction temperature (liquid sending temperature) | | Introduction pressure (liquid sending pressure) | | Fluid temperature between processing surfaces [° C.] | Discharged liquid | | Stirring of discharged liquid | | | | |
|---|---|---|---|---|---|---|---|---|---|---|---|---|---|
| | | | | | | | | | | Additive | | Stirring condition | |
| | | | | | | | | | Type | Ratio against iron oxide [%] | Temp [° C.] | Time [h] | pH after stirring |
| | | Liquid A [° C.] | Liquid B [° C.] | Liquid A [MPaG] | Liquid B [MPaG] | | pH | Temp. [° C.] | | | | | |
| Example | 1 | 146 | 108 | 0.400 | 0.42 | 143.47 | 8.66 | 20.2 | No stirring treatment | | | | |
| | 2 | | | | | | | | No additive | 100 | 100 | 1 | 10.91 |
| | 3 | | | | | | | | SDS | 100 | 100 | 1 | 9.09 |
| | 4 | 146 | 106 | 0.413 | 0.42 | 143.42 | 6.23 | 20.2 | No stirring treatment | | | | |
| | 5 | 146 | 106 | 0.412 | 0.42 | 143.33 | 8.31 | 20.2 | No stirring treatment | | | | |
| | 6 | 146 | 106 | 0.411 | 0.42 | 143.25 | 9.95 | 20.2 | No stirring treatment | | | | |
| | 7 | 146 | 106 | 0.411 | 0.42 | 143.25 | 12.34 | 20.2 | No stirring treatment | | | | |
| | 8 | 146 | 106 | 0.411 | 0.42 | 143.17 | 13.68 | 20.2 | No stirring treatment | | | | |
| Comparative Example | 1 | Reagent α-ferric oxide (Kanto Chemical Co., Inc.) | | | | | | | | | | | |
| | 2 | 146 | 106 | 0.400 | 0.42 | 143.47 | 8.66 | 20.2 | HEC | 100 | 100 | 1 | 5.31 |
| | 3 | 146 | 106 | 0.400 | 0.42 | 143.47 | 8.66 | 20.2 | NaOH | 1.2 | 100 | 1 | >14 |
| | 4 | 146 | 108 | 0.400 | 0.42 | 143.63 | 2.73 | 22.2 | No stirring treatment | | | | |
| | 5 | | | | | | | | No additive | 100 | 100 | 1 | 4.98 |
| | 6 | | | | | | | | SDS | 100 | 100 | 1 | 5.16 |
| | 7 | 146 | 106 | 0.411 | 0.42 | 143.75 | 5.04 | 20.2 | No stirring treatment | | | | |
| | 8 | 146 | 106 | 0.411 | 0.42 | 143.92 | >14 | 20.2 | No stirring treatment | | | | |
| | 9 | 56 | 79 | 0.056 | 0.12 | 57.53 | 8.91 | 20.2 | No stirring treatment | | | | |
| | 10 | 65 | 79 | 0.057 | 0.12 | 65.93 | 8.99 | 20.2 | No stirring treatment | | | | |

TABLE 2

| | | pH after treatment | Ratio of single crystal [%] | Average primary particle diameter D1 [nm] | Volume average particle diameter D2 [nm] | Haze [%] | Transmittance | | Molar absorption coefficient | |
|---|---|---|---|---|---|---|---|---|---|---|
| | | | | | | | 420 nm [%] | 650-800 nm Pass or Not | 400 nm [L/(mol · cm)] | 220 nm [L/(mol · cm)] |
| Example | 1 | 8.66 | 90.9 | 8.40 | 28.9 | 0.00 | 1.94 | Pass | 931 | 3575 |
| | 2 | 10.91 | 99.1 | 8.50 | 27.6 | 0.00 | 0.77 | Pass | 793 | 3481 |
| | 3 | 9.09 | 90.9 | 9.90 | 34.6 | 1.12 | 1.73 | Pass | 515 | 3114 |
| | 4 | 6.23 | 91.3 | 22.30 | 39.6 | 0.09 | 1.48 | Pass | 612 | 3412 |
| | 5 | 8.31 | 100 | 7.69 | 14.9 | 0.00 | 0.64 | Pass | 1008 | 3781 |
| | 6 | 9.95 | 100 | 8.19 | 16.9 | 0.00 | 0.69 | Pass | 974 | 3694 |
| | 7 | 12.34 | 99.8 | 8.69 | 17.9 | 0.00 | 0.59 | Pass | 961 | 3591 |
| | 8 | 13.68 | 94.6 | 15.60 | 24.9 | 0.10 | 1.79 | Pass | 647 | 3324 |
| Comparative Example | 1 | — | 0 | 119.60 | 125.4 | 21.90 | 23.90 | Not | 121 | 109 |
| | 2 | 5.31 | 23.2 | 29.90 | 59.1 | 2.96 | 3.99 | Not | 314 | 2841 |
| | 3 | >14 | 29.6 | 35.90 | 84.1 | 3.56 | 11.25 | Not | 296 | 2514 |
| | 4 | 2.73 | 31.2 | 26.40 | 50.9 | 2.36 | 3.12 | Not | 412 | 2412 |
| | 5 | 4.98 | 76.4 | 27.90 | 51.2 | 2.97 | 3.16 | Not | 312 | 2631 |
| | 6 | 5.16 | 67.4 | 29.30 | 52.3 | 2.98 | 4.54 | Not | 298 | 1948 |
| | 7 | 5.04 | 26.9 | 31.20 | 61.2 | 2.97 | 2.79 | Not | 312 | 2647 |
| | 8 | >14 | 11.4 | 26.40 | 65.4 | 3.12 | 3.09 | Not | 219 | 2123 |
| | 9 | 8.91 | — | — | 113.6 | 2.97 | 2.39 | Not | 116 | 1128 |
| | 10 | 8.99 | — | — | 105.4 | 2.58 | 3.06 | Not | 119 | 1564 |

Figure 3:
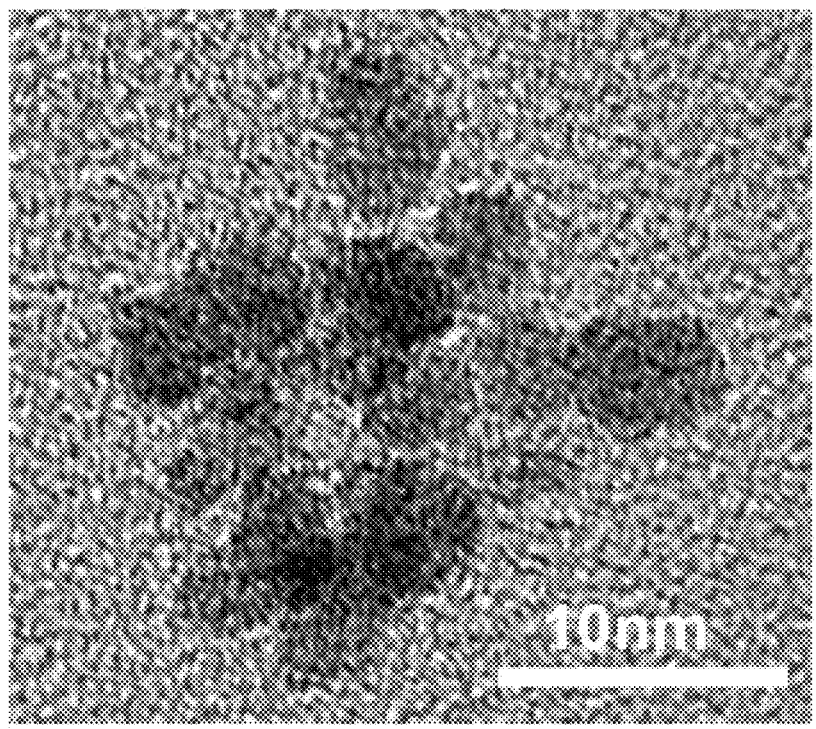
FIG. 3 shows a TEM photograph of the iron oxide particles obtained in Example 1.

FIG. 3 shows a TEM photograph of the iron oxide particles obtained in Example 1. The primary particles were substantially spherical, and their average primary particle diameter was 8.40 nm. As the result of particle size distribution measurement of the iron oxide microparticle dispersion obtained in Example 1, the volume average particle diameter was 28.9 nm, and the haze value was 0.00%. In the present invention, substantially spherical refers to practically spherical, and particularly means the shape in which the ratio of short axis to long axis is in the range of 0.5 to 1.0 when particle shape is determined by long axis and short axis.

Figure 4:
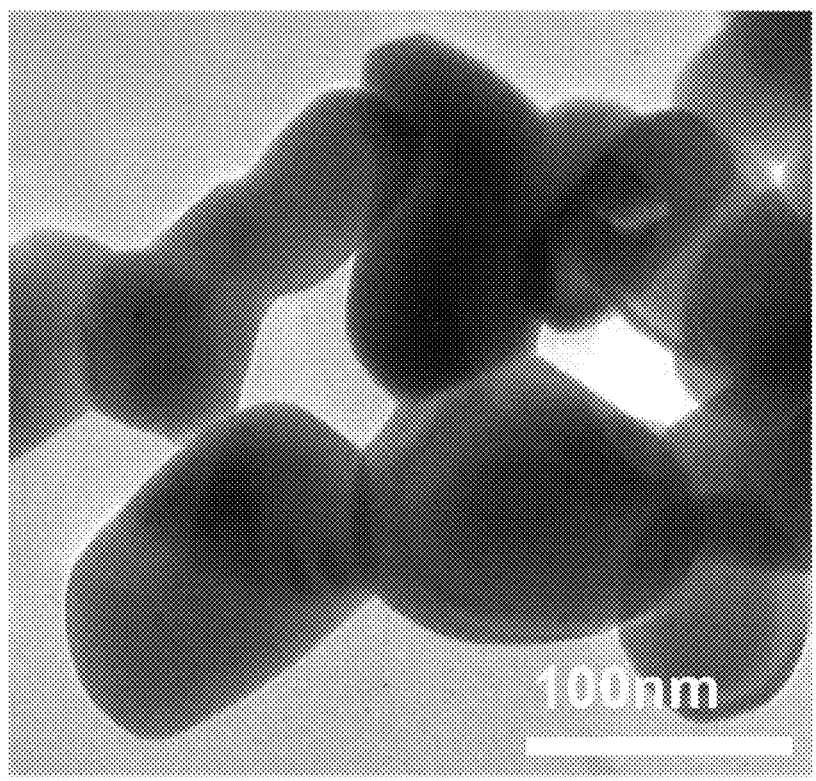
FIG. 4 shows a TEM photograph of the iron oxide particles of Comparative Example 1.

FIG. 4 shows a TEM photograph of the iron oxide particles of Comparative Example 1. The average primary particle size was 119.6 nm. As the result of particle size distribution measurement of the iron oxide microparticle dispersion obtained in Comparative Example 1, the volume average particle diameter was 125.4 nm, and haze value was 21.9%.

Figure 5:
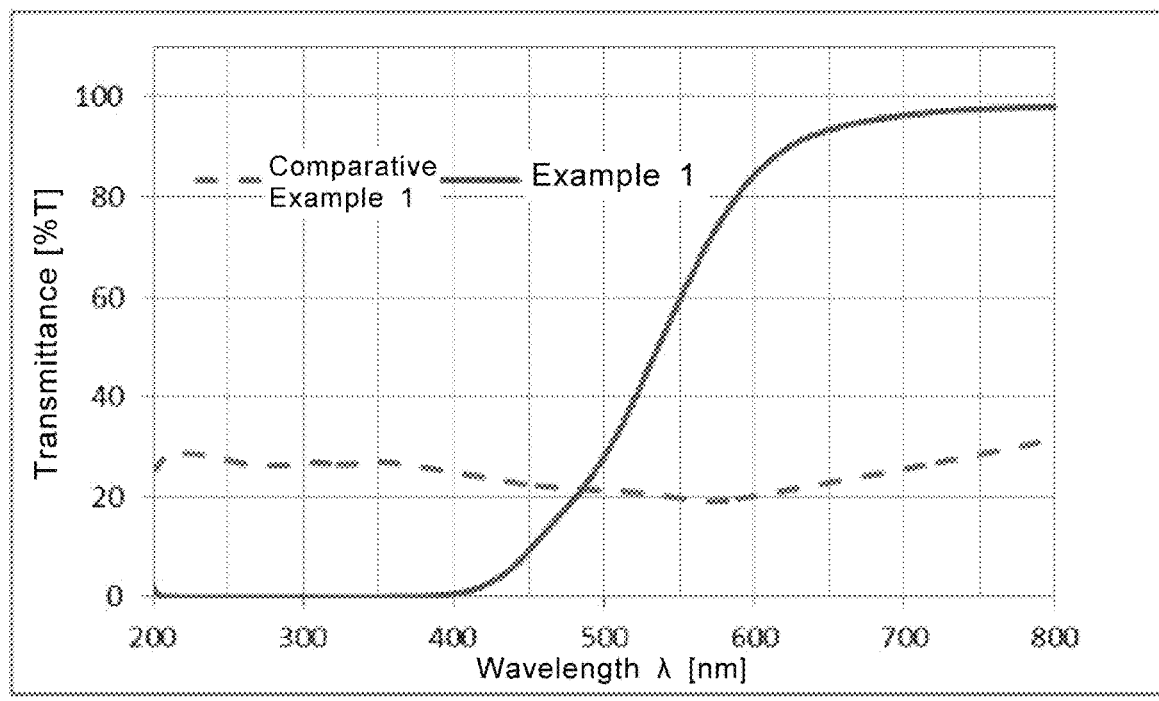
FIG. 5 shows an ultraviolet-visible transmission spectrum of the iron oxide microparticle dispersion obtained in Example 1.
Figure 6:
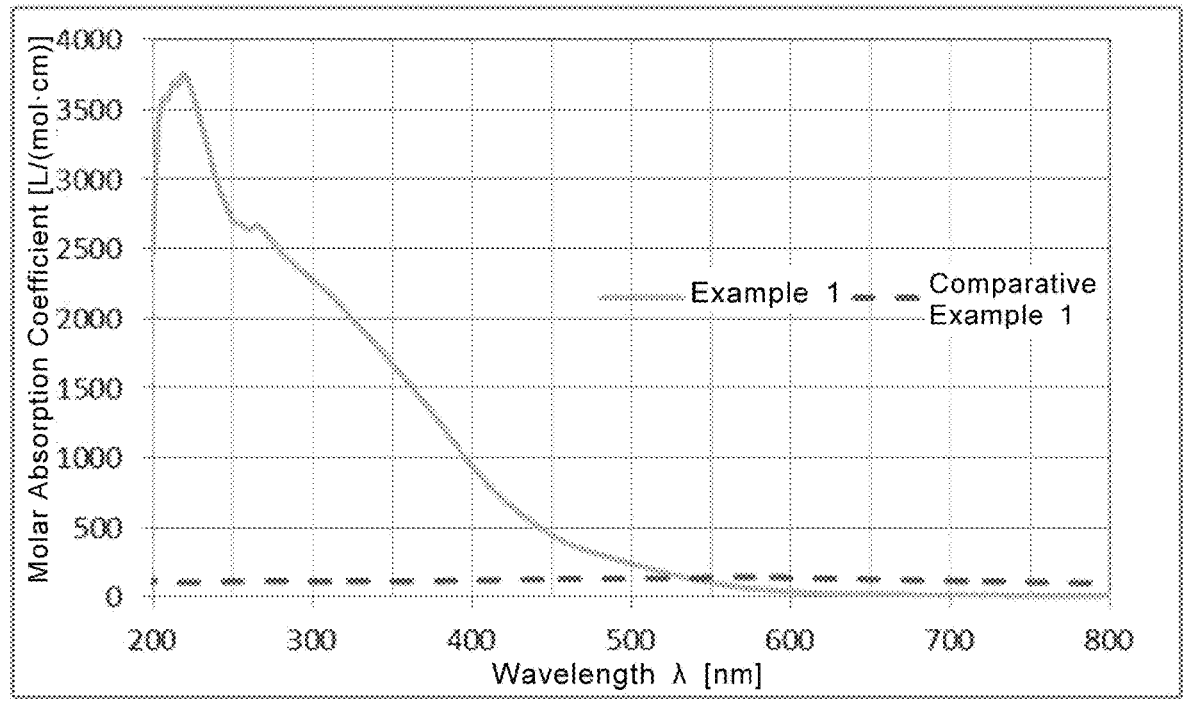
FIG. 6 shows a graph showing a molar absorption coefficient of the iron oxide microparticle dispersion obtained in Example 1 for the measurement wavelength.

FIG. 5 and FIG. 6 show respectively an ultraviolet-visible transmission spectrum and a graph showing a molar absorption coefficient of the iron oxide microparticle dispersion obtained in Example 1, respectively together with the measurement results of the iron oxide microparticle dispersion obtained in Comparative Example 1. As seen in FIG. 5, the iron oxide microparticle dispersion obtained in Example 1 did not substantially transmit the ultraviolet light of the wavelengths of 200 to 400 nm, and the transmittance for the wavelength of 420 nm was 1.94%. Furthermore, it was found that the transmittance for the wavelengths of 650 to 800 nm was more than 80%. That is, it was found that in the entire measurement range, the light of the wavelengths of 200 to 420 nm was absorbed, and the other light, in particular, the light of 650 to 800 nm was transmitted. In contrast, the transmittance of the iron oxide microparticle dispersion of Comparative Example 1 was generally 20 to 30% in the entire measurement range, and clear difference between its absorption region and its transmission region could not be observed. Also as seen in FIG. 6, the molar absorption coefficient of the iron oxide microparticles obtained in Example 1 was 931 L/(mol·cm) for the light of the wavelength of 400 nm, and 3575 L/(mol·cm) for the light of the wavelength of 220 nm. In contrast, the molar absorption coefficient of the iron oxide microparticles of Comparative Example 1 was 100 to 150 L/(mol·cm) in the entire measurement range. In the XRD measurement results, peaks of $\alpha\text{-}F_2O_3$ (hematite) were detected clearly in both Example 1 and Comparative Example 1.

Figure 7:
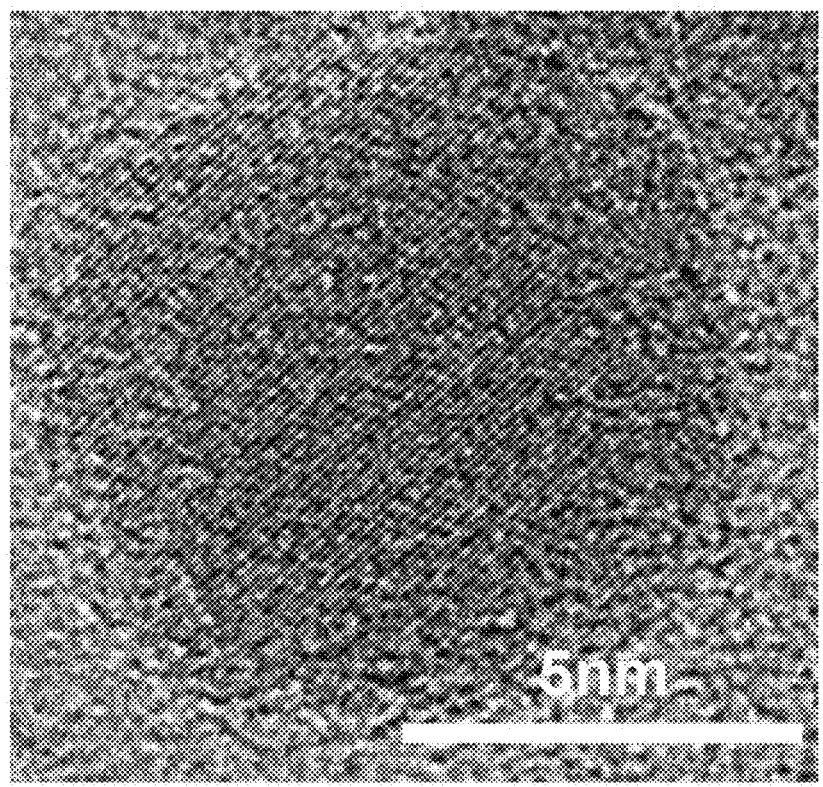
FIG. 7 shows a TEM photograph of the iron oxide particles obtained in Example 2.

Next, FIG. 7 shows a TEM photograph of the iron oxide microparticles obtained in Example 2. Interference fringes of the crystal lattice were observed in the same direction throughout the primary particles, compared with those of Example 1, and it was confirmed that the single crystals of the iron oxide microparticles were formed. The average primary particle diameter was 8.50 nm. As the result of particle size distribution measurement of the iron oxide microparticle dispersion obtained in Example 2, the volume average particle diameter was 27.6 nm, and the haze value was 0.00%.

Figure 8:
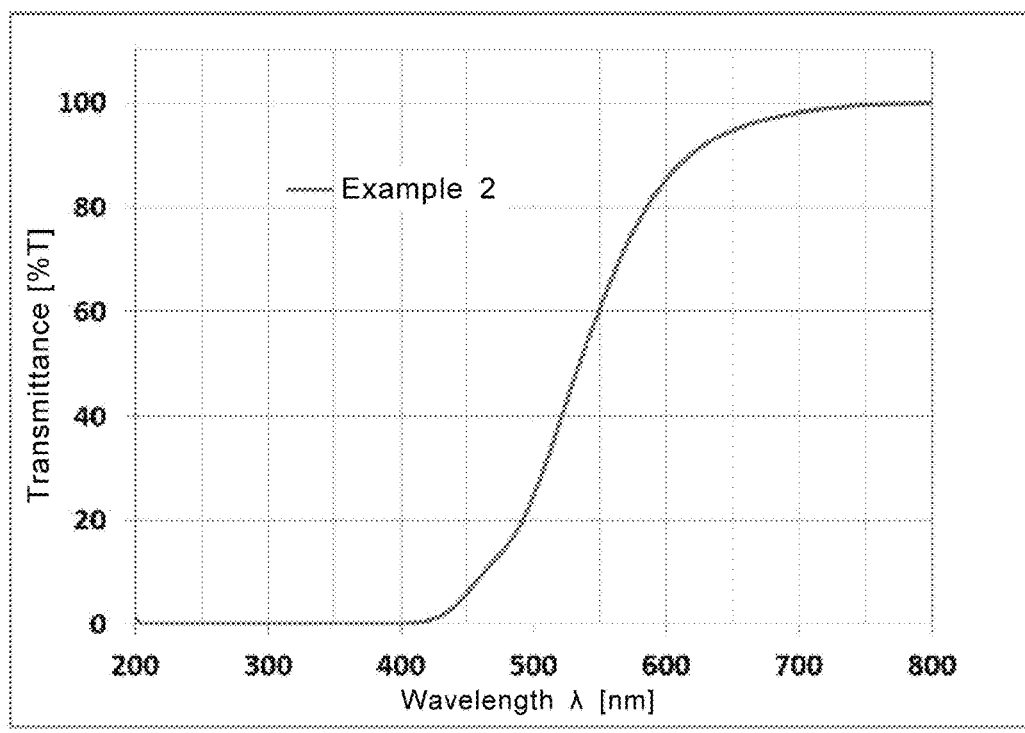
FIG. 8 shows an ultraviolet-visible transmission spectrum of the iron oxide microparticle dispersion obtained in Example 2.
Figure 9:
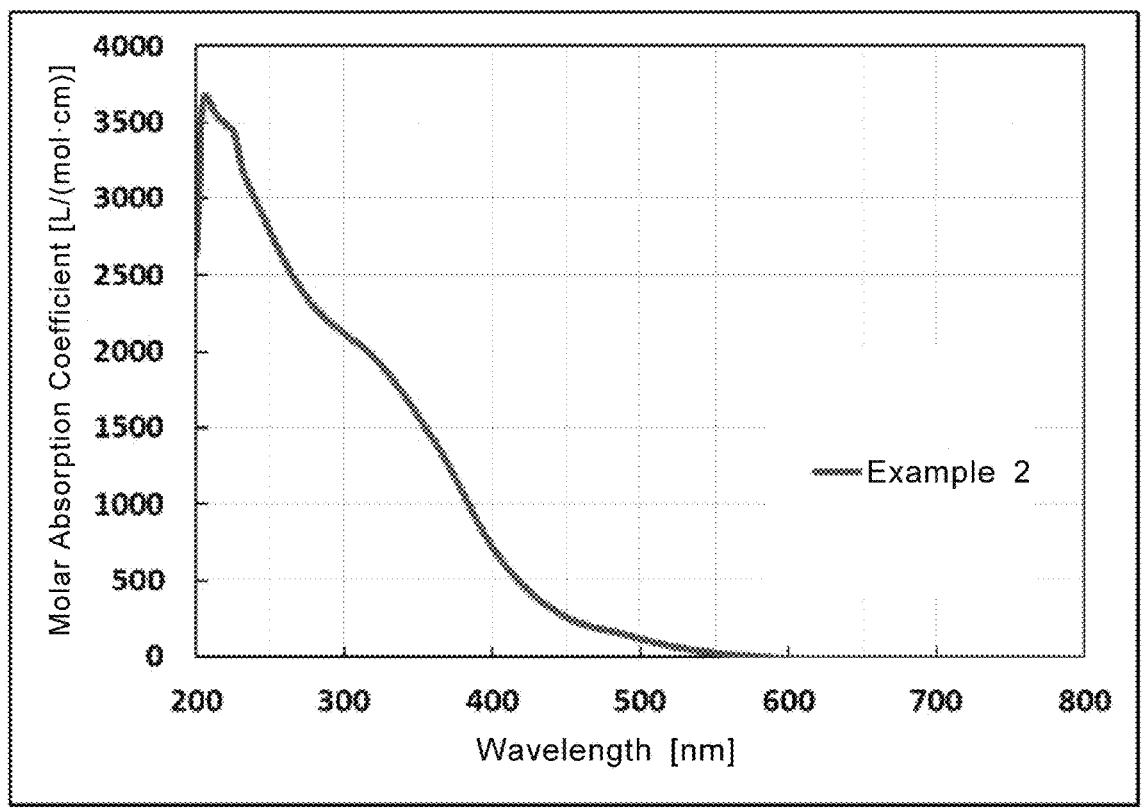
FIG. 9 shows a graph showing a molar absorption coefficient of the iron oxide microparticle dispersion obtained in Example 2 for the measurement wavelength.

FIG. 8 and FIG. 9 shows respectively an ultraviolet-visible transmission spectrum and a graph showing the molar absorption coefficient of the iron oxide microparticle dispersion obtained in Example 2. As seen in FIG. 8, the iron oxide microparticle dispersion obtained in Example 2 did not substantially transmit the ultraviolet light of the wavelengths of 200 to 400 nm, and the transmittance for the wavelength of 420 nm was 0.77%. Furthermore, it was found that the transmittance for the wavelengths of 650 to 800 nm was more than 80%. That is, it was found that in the entire measurement range, the light of the wavelengths of 200 to 420 nm was absorbed, and the other light, in particular, the light of 650 to 800 nm was transmitted. Also as seen in FIG. 9, the molar absorption coefficient of the iron oxide microparticles obtained in Example 2 was 793 L/(mol·cm) for the light of the wavelength of 400 nm, and 3481 L/(mol·cm) for the light of the wavelength of 220 nm. In the XRD measurement results, peaks of $\alpha\text{-}F_2O_3$ (hematite) were detected clearly.

From the TEM photograph of Example 3, the average primary particle size was 9.90 nm. As the result of particle size distribution measurement of the iron oxide microparticle dispersion obtained in Example 3, the volume average particle diameter was 34.6 nm, and the haze value was 1.12%. Further, from the ultraviolet-visible transmission spectrum measurement, the iron oxide microparticle dispersion obtained in Example 3 did not substantially transmit the ultraviolet light of the wavelengths of 200 to 400 nm, and the transmittance for the wavelength of 420 nm was 1.79%. Furthermore, it was found that the transmittance for the wavelengths of 650 to 800 nm was more than 80%. That is, it was found that in the entire measurement range, the light of the wavelengths of 200 to 420 nm was absorbed, and the other light, in particular, the light of 650 to 800 nm was transmitted. Also, the molar absorption coefficient of the iron oxide microparticles obtained in Example 3 was 515 L/(mol·cm) for the light of the wavelength of 400 nm, and 3114 L/(mol·cm) for the light of the wavelength of 220 nm. In the XRD measurement results, peaks of $\alpha\text{-}F_2O_3$ (hematite) were detected clearly.

From the TEM photograph of Comparative Example 2, the average primary particle size was 12.30 nm. As the result of particle size distribution measurement of the iron oxide microparticle dispersion obtained in Comparative Example 2, the volume average particle diameter was 59.1 nm, and the haze value was 2.96%. Further, from the ultraviolet-visible transmission spectrum measurement, the transmittance of the iron oxide microparticle dispersion obtained in Comparative Example 2 for the wavelength of 420 nm was 3.99%. Also, the molar absorption coefficient of the iron oxide microparticles obtained in Comparative Example 2 was 314 L/(mol·cm) for the light of the wavelength of 400 nm, and 2841 L/(mol·cm) for the light of the wavelength of 220 nm. In the XRD measurement results, it was confirmed that peaks of $\alpha\text{-}F_2O_3$ (hematite) were smaller and broader than those of Examples 1, 2 and 3.

The average primary particle size of Comparative Example 3 was 35.90 nm. As the result of particle size distribution measurement of the iron oxide microparticle dispersion obtained in Comparative Example 3, the volume average particle diameter was 84.1 nm, and the haze value was 3.56%. Further, from the ultraviolet-visible transmission spectrum measurement, the transmittance of the iron oxide microparticle dispersion obtained in Comparative Example 3 for the wavelength of 420 nm was 11.25%. Also, the molar absorption coefficient of the iron oxide microparticles obtained in Comparative Example 3 was 296 L/(mol·cm) for the light of the wavelength of 400 nm, and 2514 L/(mol·cm) for the light of the wavelength of 220 nm. In the XRD measurement results, it was confirmed that peaks of $\alpha\text{-}F_2O_3$ (hematite) were smaller and broader than those of Examples 1, 2 and 3.

Figure 10:
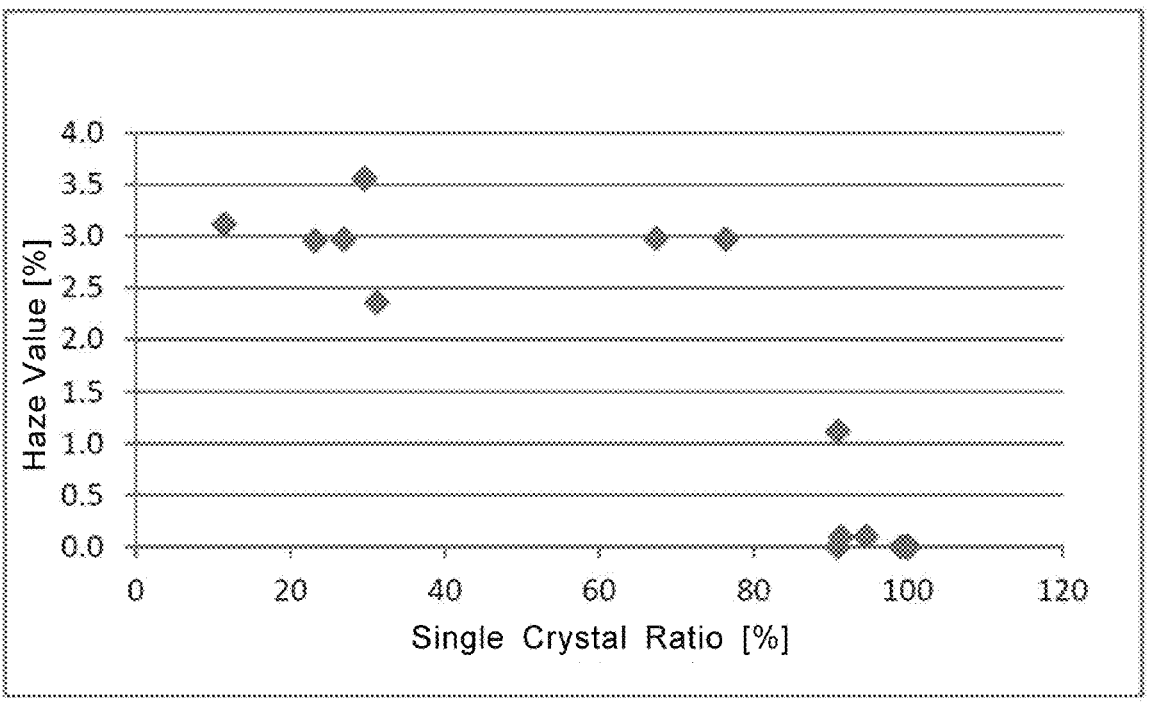
FIG. 10 shows a dispersion diagram showing the relation between single crystal ratios and haze values in Examples 1-8 and Comparative Examples 2-8.
Figure 11:
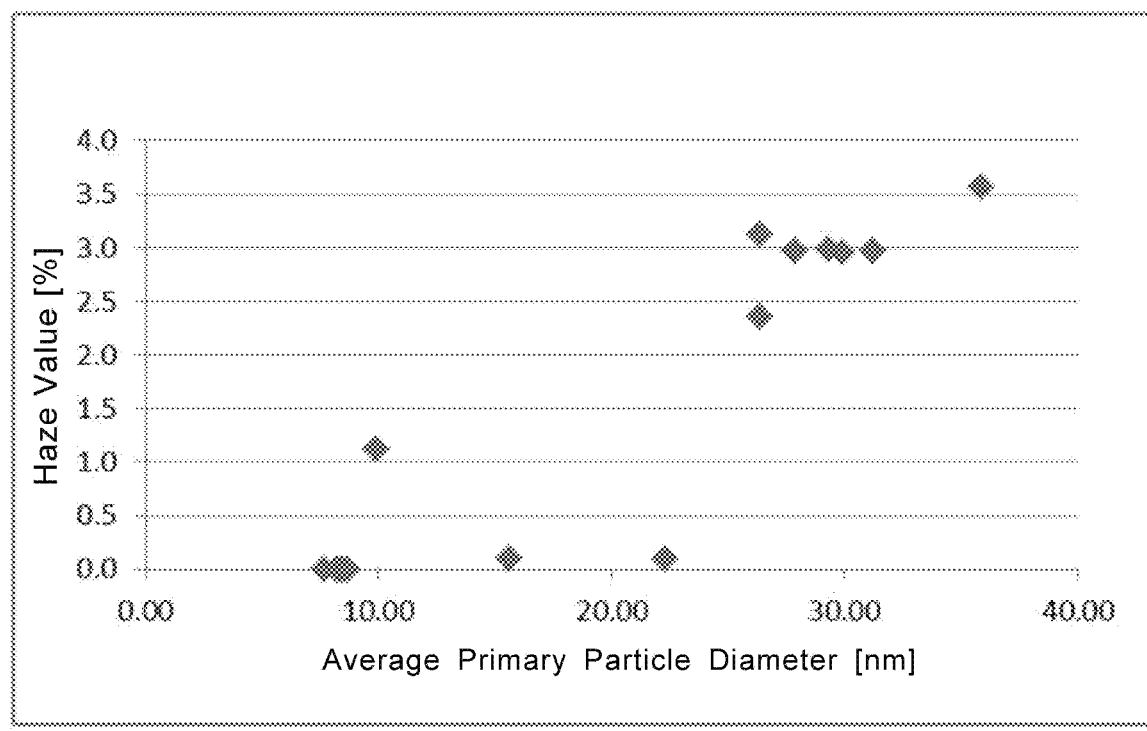
FIG. 11 shows a dispersion diagram showing the relation between average primary particle diameters and haze values in Examples 1-8 and Comparative Examples 2-8.
Figure 12:
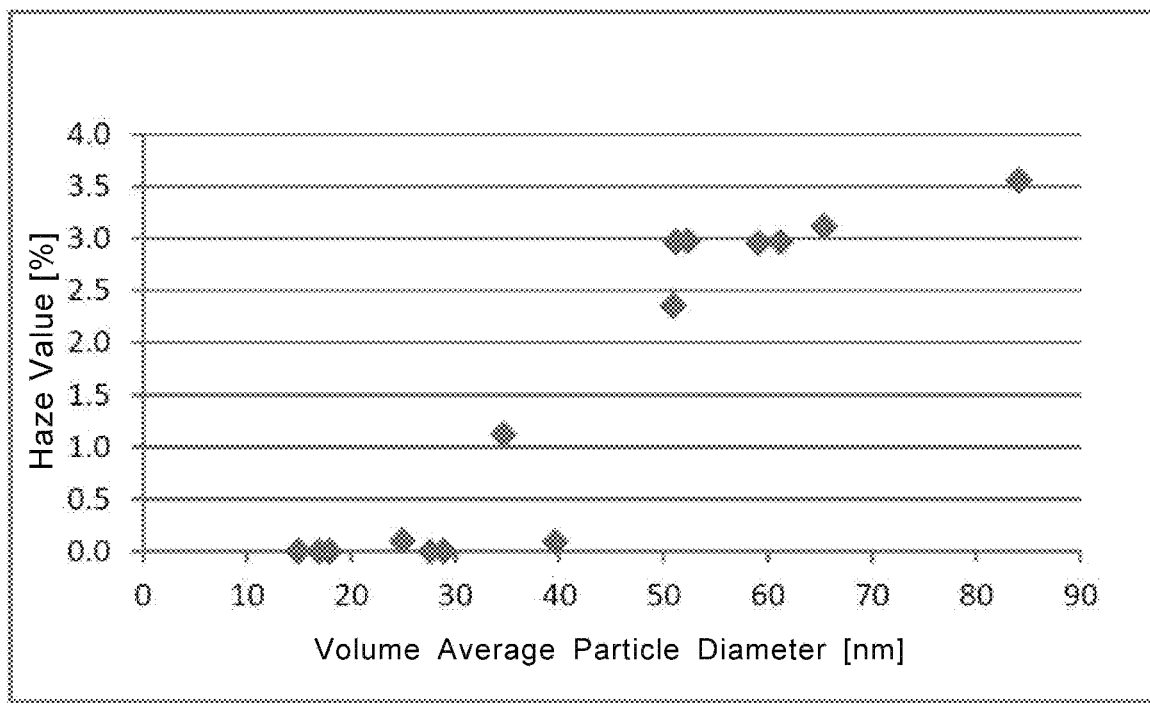
FIG. 12 shows a dispersion diagram showing the relation between secondary particle diameters (volume average particle diameters) and haze values in Examples 1-8 and Comparative Examples 2-8.

As shown in Tables described above and FIGS. 10 to 12, it is supported that haze value has a relation to single crystal ratio, average primary particle diameter and secondary particle diameter (volume average particle diameter), which is shown in the summary of the invention and the embodiments of the invention described above.

Figure 13:
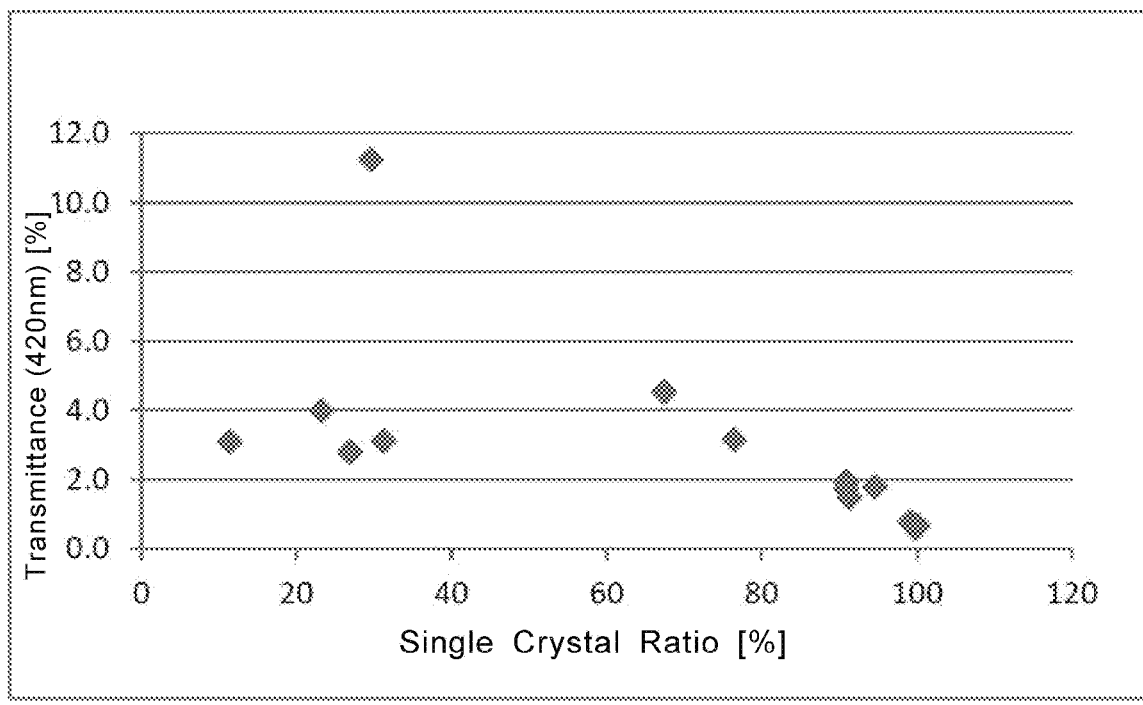
FIG. 13 shows a dispersion diagram showing the relation between single crystal ratios and transmittances in Examples 1-8 and Comparative Examples 2-8.
Figure 14:
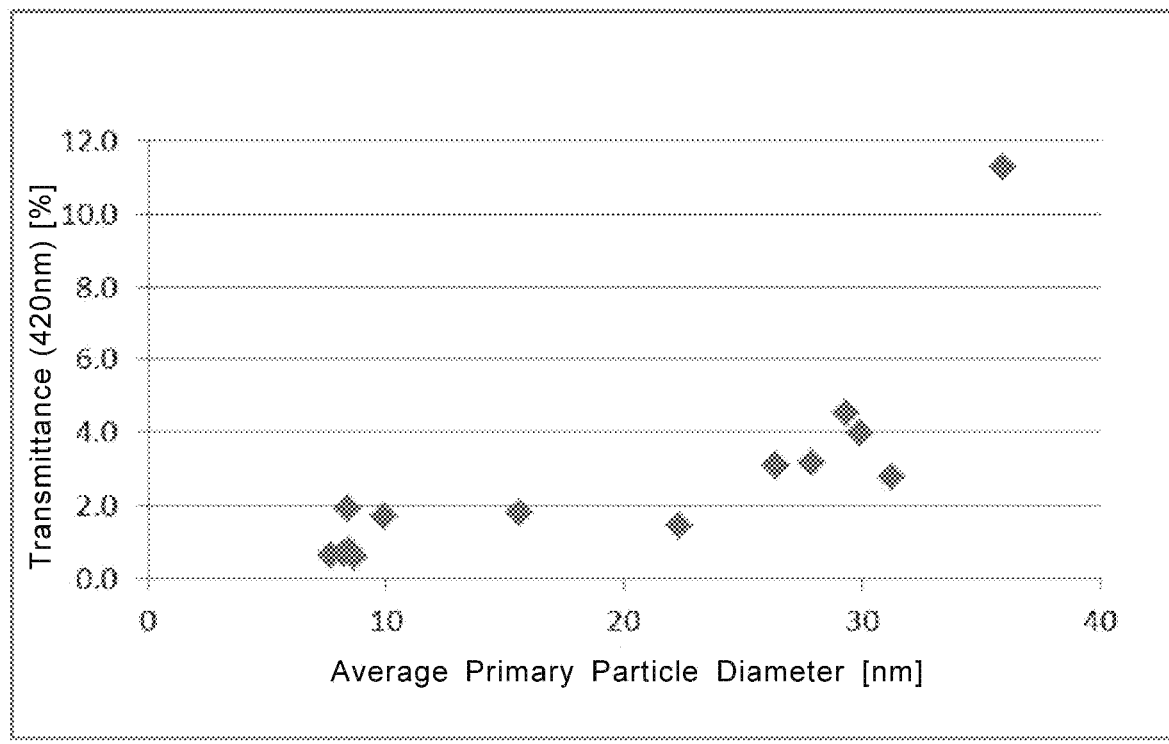
FIG. 14 shows a dispersion diagram showing the relation between average primary particle diameters and transmittances in Examples 1-8 and Comparative Examples 2-8.
Figure 15:
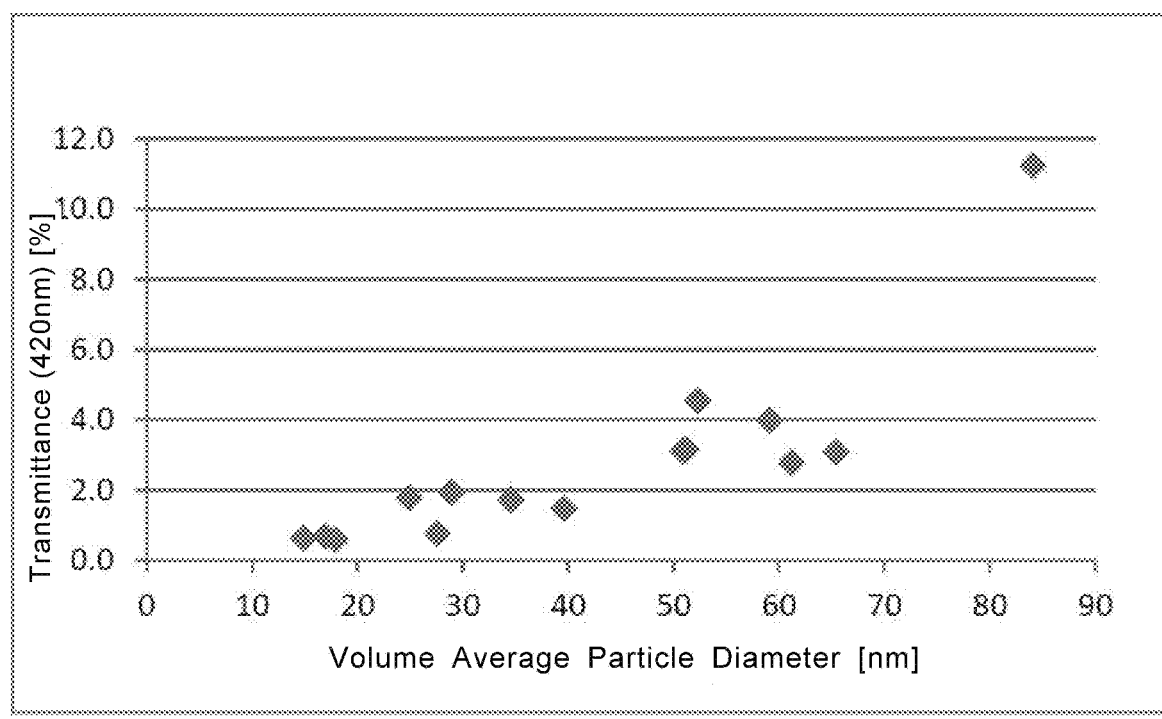
FIG. 15 shows a dispersion diagram showing the relation between secondary particle diameters (volume average particle diameters) and transmittances in Examples 1-8 and Comparative Examples 2-8.

As shown in Tables described above and FIGS. 13 to 15, it is supported that transmittance has a relation to single crystal ratio, average primary particle diameter and secondary particle diameter (volume average particle diameter), which is shown in the summary of the invention and the embodiments of the invention described above.

Figure 16:
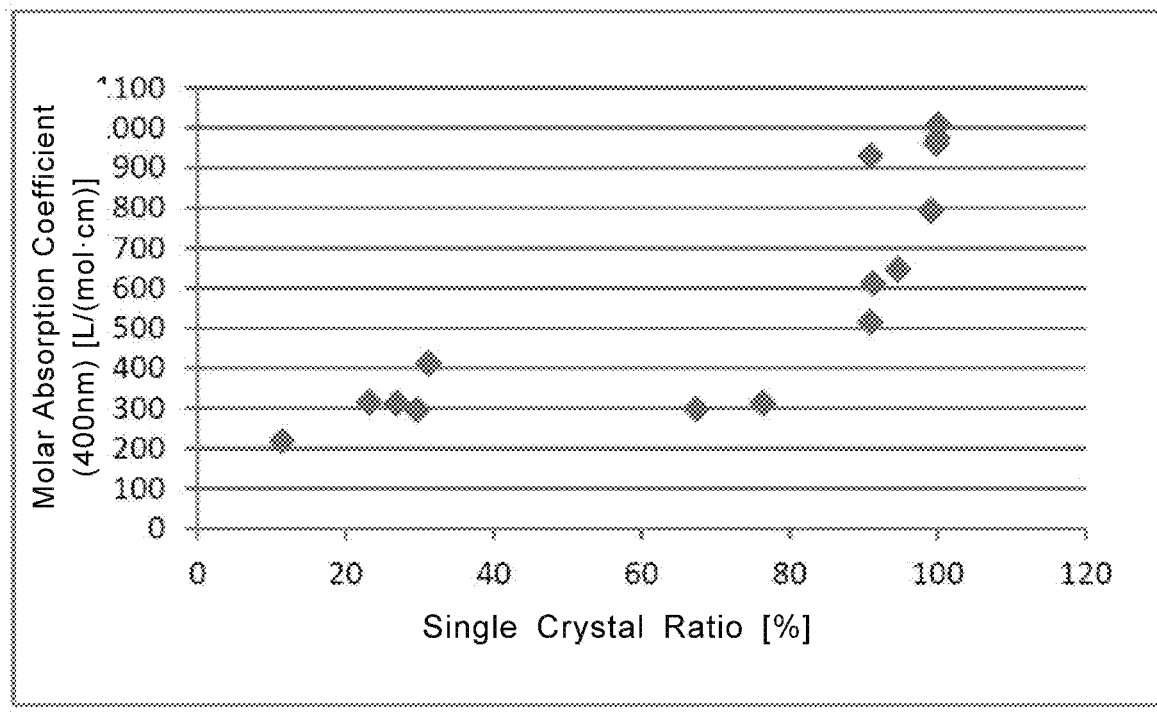
FIG. 16 shows a dispersion diagram showing the relation between single crystal ratios and molar absorption coefficients for the light of the wavelength of 400 nm in Examples 1-8 and Comparative Examples 2-8.
Figure 17:
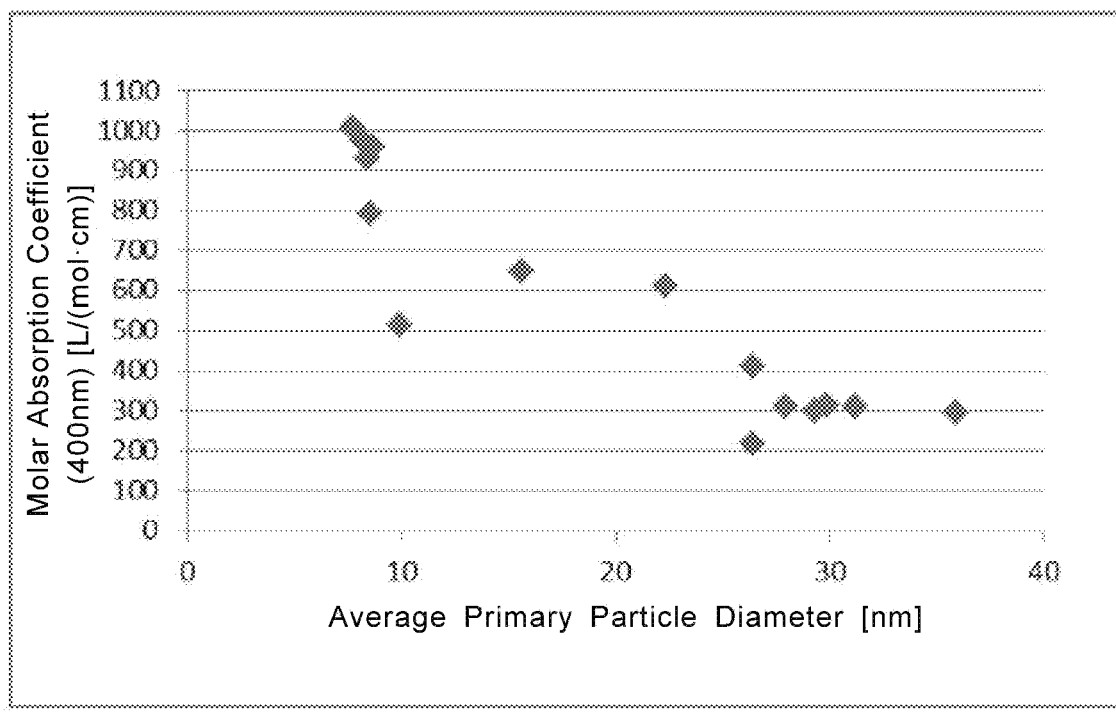
FIG. 17 shows a dispersion diagram showing the relation between average primary diameters and molar absorption coefficients for the light of the wavelength of 400 nm in Examples 1-8 and Comparative Examples 2-8.
Figure 18:
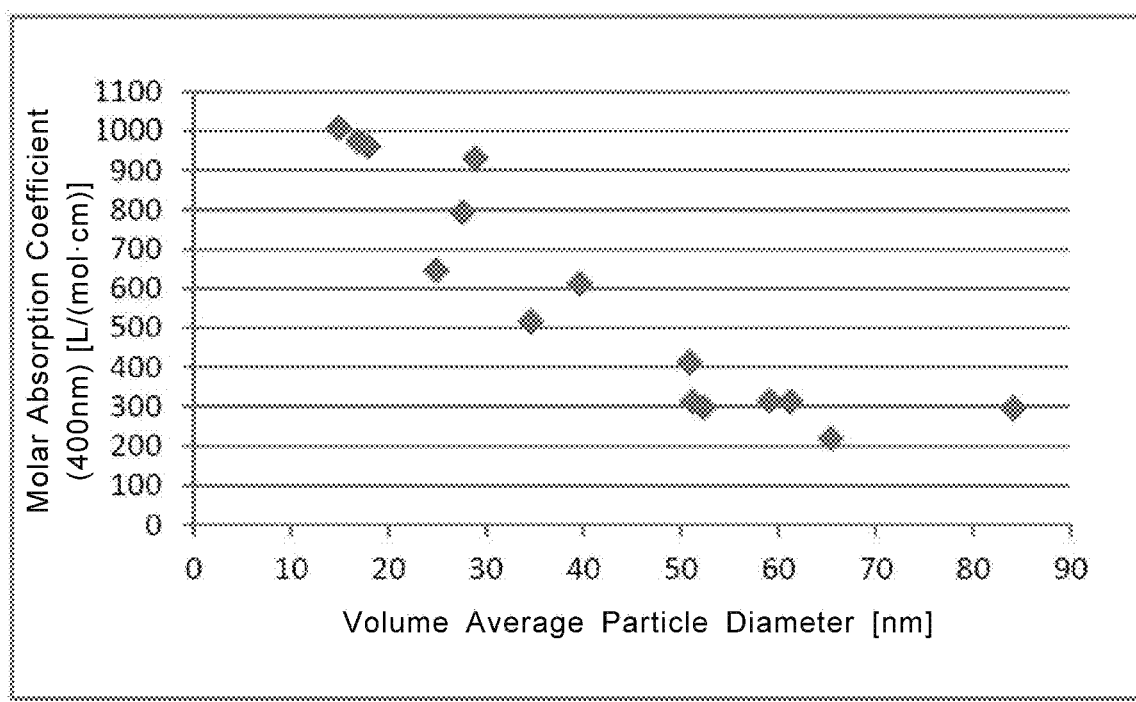
FIG. 18 shows a dispersion diagram showing the relation between secondary particle diameters (volume average particle diameters) and molar absorption coefficients for the light of the wavelength of 400 nm in Examples 1-8 and Comparative Examples 2-8.

As shown in Tables described above and FIGS. 16 to 18, it is supported that a molar absorption coefficient for the light of the wavelength of 400 nm has a relation to single crystal ratio, average primary particle diameter and secondary particle diameter (volume average particle diameter), which is shown in the summary of the invention and the embodiments of the invention described above.

Figure 19:
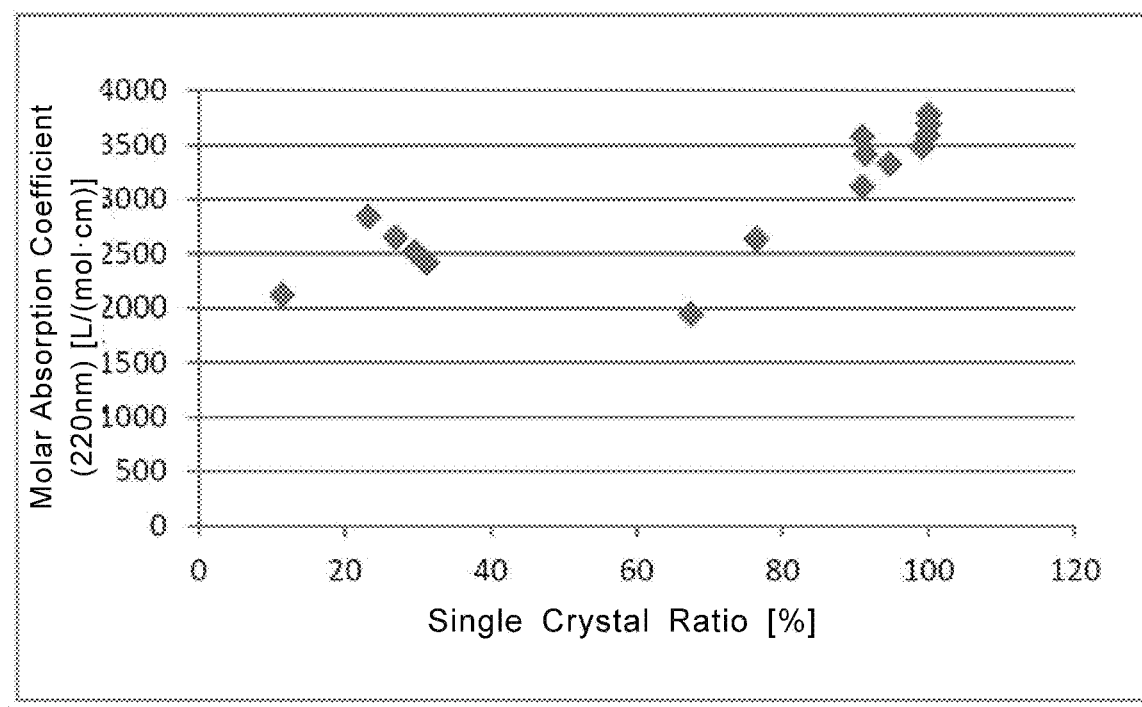
FIG. 19 shows a dispersion diagram showing the relation between single crystal ratios and molar absorption coefficients for the light of the wavelength of 220 nm in Examples 1-8 and Comparative Examples 2-8.
Figure 20:
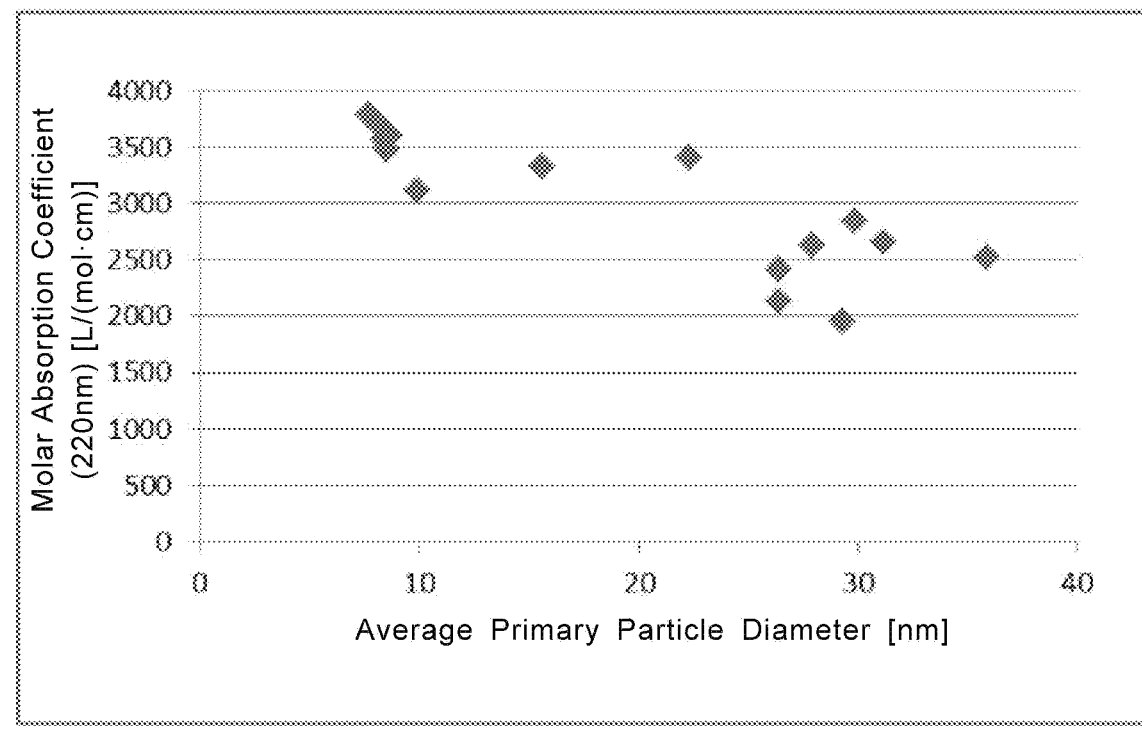
FIG. 20 shows a dispersion diagram showing the relation between average primary diameters and molar absorption coefficients for the light of the wavelength of 220 nm in Examples 1-8 and Comparative Examples 2-8.
Figure 21:
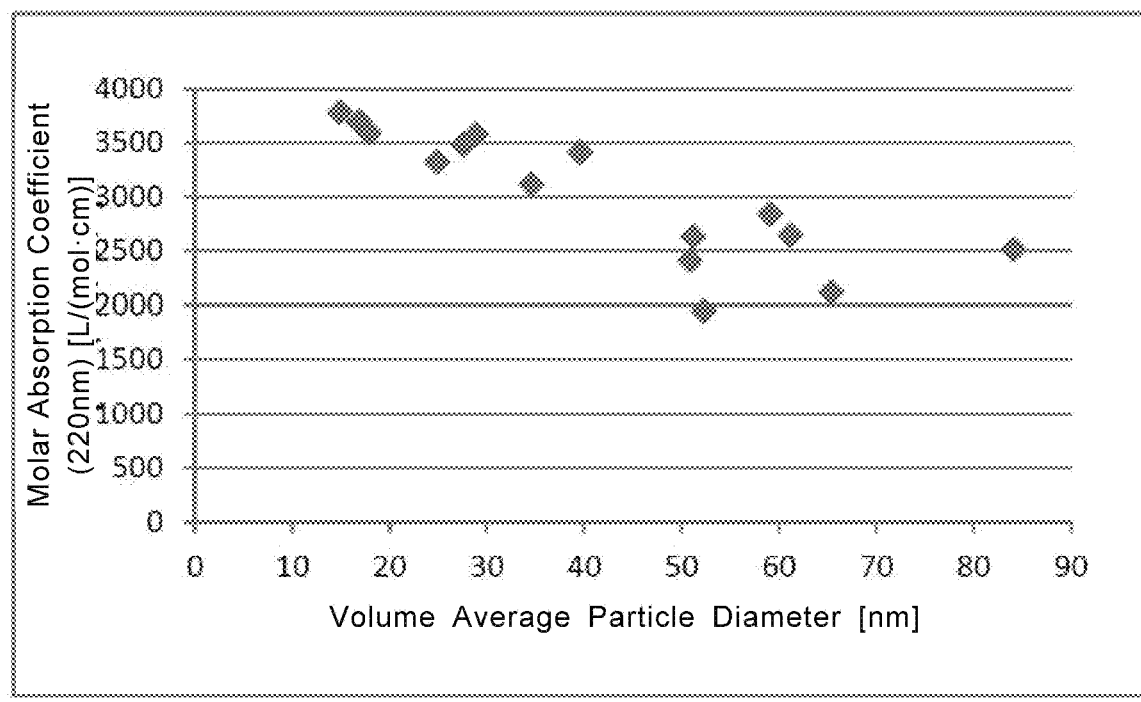
FIG. 21 shows a dispersion diagram showing the relation between secondary particle diameters (volume average particle diameters) and molar absorption coefficients for the light of the wavelength of 220 nm in Examples 1-8 and Comparative Examples 2-8.

As shown in Tables described above and FIGS. 19 to 21, it is supported that a molar absorption coefficient for the light with the wavelength of 220 nm has a relation to single crystal ratio, average primary particle diameter and secondary particle diameter (volume average particle diameter), which is shown in the summary of the invention and the embodiments of the invention described above.

Figure 22:
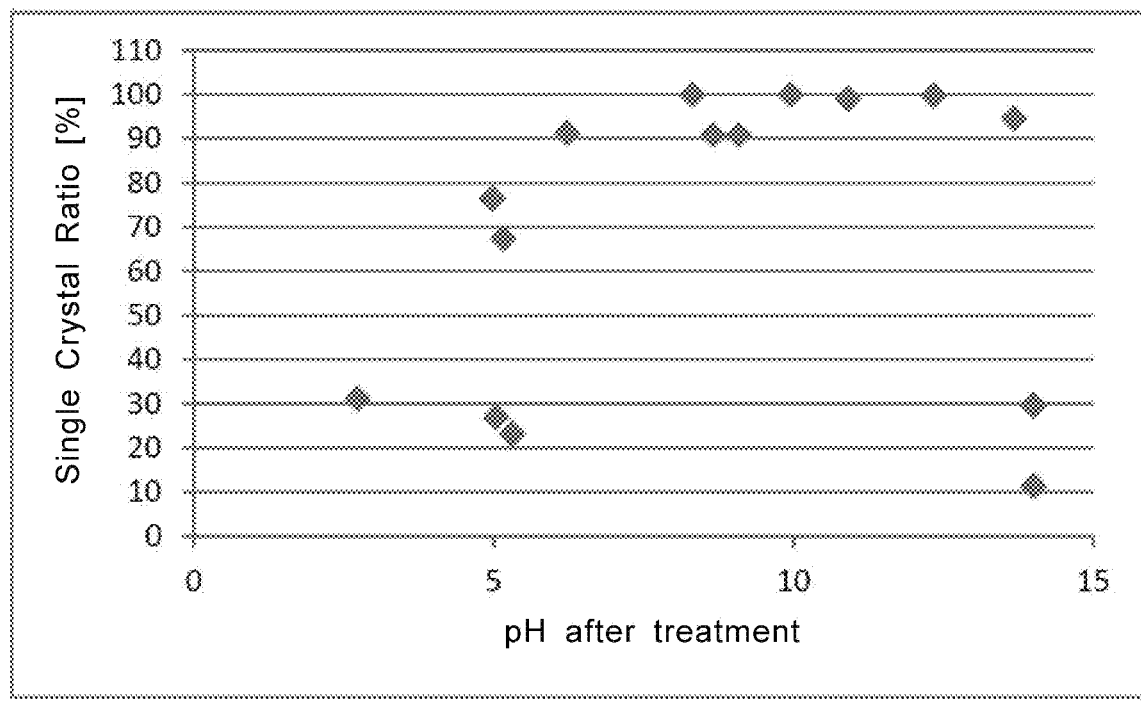
FIG. 22 shows a dispersion diagram showing the relation between pH after treatment in step (a) or step (a-2) and single crystal ratios in Examples 1-8 and Comparative Examples 2-8.
Figure 23:
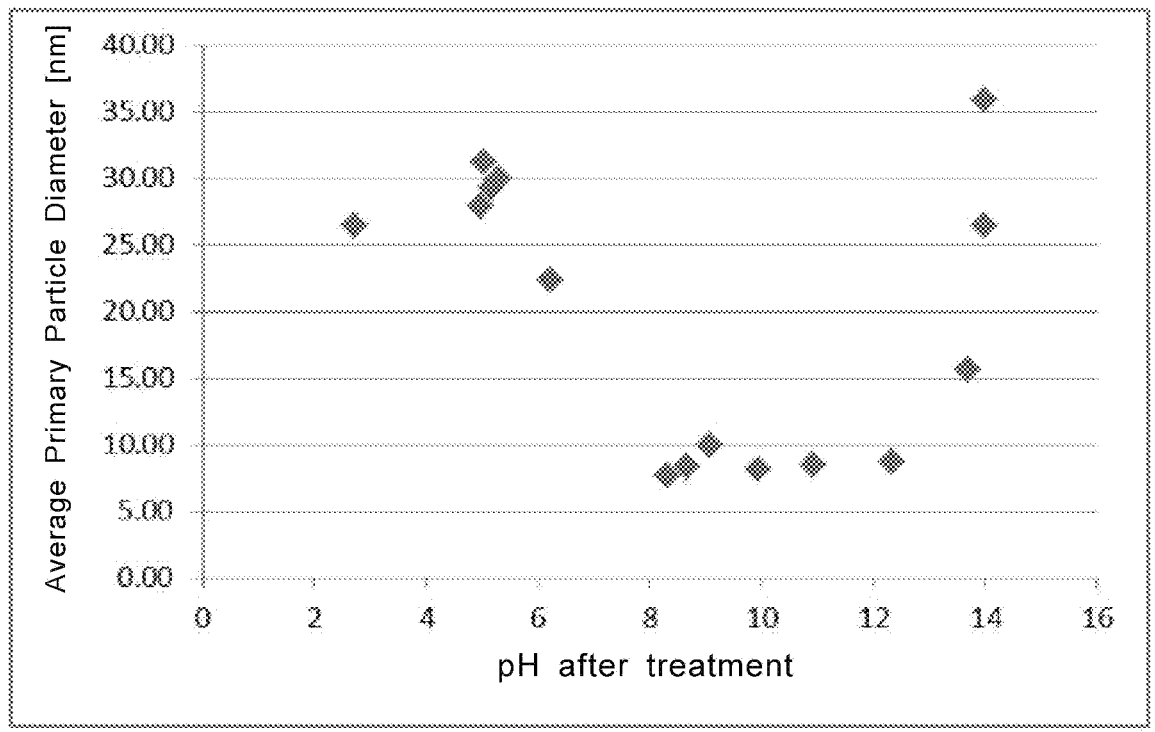
FIG. 23 shows a dispersion diagram showing the relation between pH after treatment in step (a) or step (a-2) and average primary particle sizes in Examples 1-8 and Comparative Examples 2-8.
Figure 24:
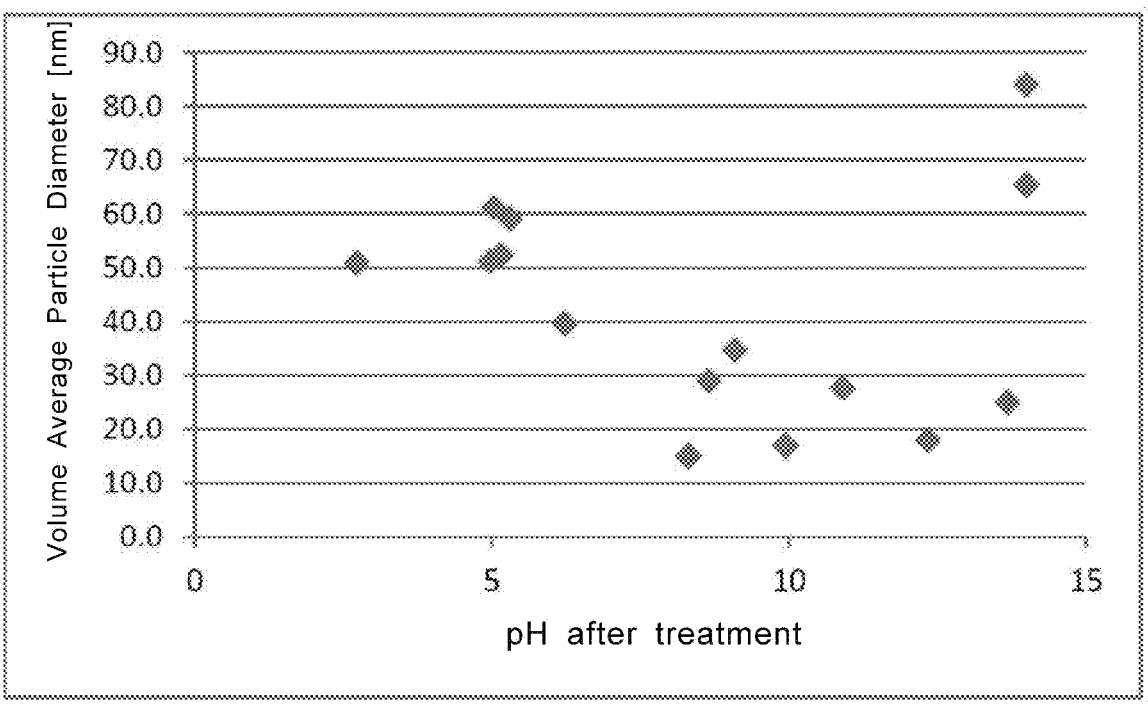
FIG. 24 shows a dispersion diagram showing the relation between pH after treatment in step (a) or step (a-2) and secondary particle diameters (volume average particle diameters) in Examples 1-8 and Comparative Examples 2-8.

As shown in Tables described above and FIGS. 22 to 24, it is supported that pH after treatment of step (a) or step (a-2) has a relation to single crystal ratio, average primary particle diameter and secondary particle diameter (volume average particle diameter), which is shown in the summary of the invention and the embodiments of the invention described above.

It was found that the iron oxide microparticles dispersions obtained in the examples are ultraviolet protective agent compositions which have high transparency and excellent protection ability against a light of ultraviolet region of wavelengths of 200 to 420 nm.

REFERENCE SIGNS LIST 1 the first processing surface
2 the second processing surface
10 the first processing unit
11 the first holder
20 the second processing unit
21 the second holder
d1 the first introduction part
d2 the second introduction part
d20 opening

The invention claimed is:

1. An ultraviolet protective agent composition obtained by dispersing iron oxide microparticles in a dispersion medium,
wherein the iron oxide is α-hematite,
wherein a primary particle diameter of the iron oxide microparticles is less than 25 nm, and more than 90% of the iron oxide microparticles are single crystals,
wherein the iron oxide microparticles of single crystals are microparticles in which lattice strips are observed in one direction in the electron microscopic observation, and
wherein a haze value of a dispersion of the iron oxide microparticles is 2.0% or less, and a transmittance of the dispersion of the iron oxide microparticles for the light of the wavelengths of 200 to 420 nm is 2.0% or less.

2. The ultraviolet protective agent composition according to claim 1, wherein the iron oxide microparticles are microparticles obtained by the following steps:
as a microreactor is used a fluid processing machine equipped with a first processing surface and a second processing surface which are disposed so as to face each other, being capable of approaching to and separating from each other, at least one of which rotates relatively to the other;
at least two fluids to be processed of an iron oxide raw material fluid and an iron oxide precipitation fluid are introduced between the first processing surface and the second processing surface;
a separation force acting in the direction of separating the first processing surface and the second processing surface is generated by an introduction pressure of the fluids to be processed between the first processing surface and the second processing surface, so that the interval between the first processing surface and the second processing surface is maintained minute by a pressure balance between the separation force and a force applied in the direction of approximating the first processing surface and the second processing surface;
the at least two fluids to be processed are merged between the first processing surface and the second processing surface which are maintained with the minute interval, and are passed between the first processing surface and the second processing surface, to form a thin film fluid; and
the at least two fluids to be processed are mixed in the thin film fluid to precipitate the iron oxide microparticles, and the fluid to be processed is discharged from the space between the first processing surface and the second processing surface, and pH of the fluid discharged from the space between the first processing surface and the second processing surface is made to be 6 to 14, to obtain the microparticles.

3. The ultraviolet protective agent composition according to claim 2,
wherein the introduction pressure of both fluids to be processed of the iron oxide raw material fluid and the iron oxide precipitation fluid exceeds the standard pressure, and
the temperature of the iron oxide raw material fluid to be introduced between the processing surfaces is higher than the normal boiling point of the iron oxide raw material fluid, and is lower than the boiling point under the introduction pressure.

4. The ultraviolet protective agent composition according to claim 1, wherein the iron oxide microparticles are microparticles obtained by the following steps:
as a microreactor is used a fluid processing machine equipped with a first processing surface and a second processing surface which are disposed so as to face each other, being capable of approaching to and separating from each other, at least one of which rotates relatively to the other;
at least two fluids to be processed of an iron oxide raw material fluid and an iron oxide precipitation fluid are introduced between the first processing surface and the second processing surface;
a separation force acting in the direction of separating the first processing surface and the second processing surface is generated by an introduction pressure of the fluids to be processed between the first processing surface and the second processing surface, so that the interval between the first processing surface and the second processing surface is maintained minute by a pressure balance between the separation force and the force applied in the direction of approximating the first processing surface and the second processing surface;
the at least two fluids to be processed are merged between the first processing surface and the second processing surface which are maintained with the minute interval, and are passed between the first processing surface and the second processing surface, to form a thin film fluid;
the at least two fluids to be processed are mixed in the thin film fluid to precipitate the iron oxide microparticles, and the fluid to be processed is discharged from the space between the first processing surface and the second processing surface; and
an additional stirring treatment is performed to the fluid discharged from the space between the first processing surface and the second processing surface, and pH of the fluid discharged from the space between the first processing surface and the second processing surface after the stirring treatment is made to be 6 to 14, to obtain the microparticles.

5. A method of producing an ultraviolet protective agent composition, which comprises at least
step (a) of precipitating iron oxide microparticles by mixing with a microreactor an iron oxide raw material fluid containing at least $Fe^{3+}$ ion, and an iron oxide precipitation fluid containing at least a basic substance, and
step (b) of dispersing the above precipitated iron oxide microparticles in a dispersion medium to obtain a dispersion of the iron oxide microparticles, wherein:

the iron oxide is α-hematite, a primary particle diameter of the iron oxide microparticles is less than 25 nm, and more than 90% of the iron oxide microparticles are single crystals, the iron oxide microparticles of single crystals are microparticles in which lattice strips are observed in one direction in the electron microscopic observation, and a haze value of the dispersion of the iron oxide microparticles is 2.0% or less, and a transmittance of the dispersion of the iron oxide microparticles for the light of the wavelengths of 200 to 420 nm is 2.0% or less.

6. The method of producing an ultraviolet protective agent composition according to claim 5, wherein a transmittance of the dispersion of the iron oxide microparticles for the light of the wavelengths of 650 to 800 nm is 80% or more.

7. The method of producing an ultraviolet protective agent composition according to claim 5, wherein a secondary particle diameter of the iron oxide microparticles is 50 nm or less.

8. The method of producing an ultraviolet protective agent composition according to claim 5, wherein a molar absorption coefficient of the dispersion of the iron oxide microparticles for the light of the wavelength of 400 nm is 500 L/(mol·cm) or more, and a molar absorption coefficient of the dispersion of the iron oxide microparticles for the light of the wavelength of 220 nm is 3000 L/(mol·cm) or more.

9. The method of producing an ultraviolet protective agent composition according to claim 5, wherein the iron oxide microparticles comprise substantially spherical iron oxide microparticles.

10. The method of producing an ultraviolet protective agent composition according to claim 5, wherein the iron oxide microparticles comprise single crystals of iron oxide microparticles.

11. The method of producing an ultraviolet protective agent composition according to claim 5, wherein as a microreactor is used a fluid processing machine equipped with the first processing surface and the second processing surface which are disposed so as to face each other, being capable of approaching to and separating from each other, at least one of which rotates relatively to the other;

at least two kinds of fluids to be processed of the iron oxide raw material fluid and the iron oxide precipitation fluid are introduced between the first processing surface and the second processing surface;

a separation force acting in the direction of separating the first processing surface and the second processing surface is generated by an introduction pressure of the fluids to be processed between the first processing surface and the second processing surface, so that the interval between the first processing surface and the second processing surface is maintained minute by a pressure balance between the separation force and the force applied in the direction of approximating the first processing surface and the second processing surface;

the at least two fluids to be processed are merged between the first processing surface and the second processing surface which are maintained with the minute interval, and are passed between the first processing surface and the second processing surface, to form a thin film fluid; and the fluids to be processed are mixed in the thin film fluid to precipitate the iron oxide microparticles.

12. The method of producing an ultraviolet protective agent composition according to claim 11, wherein the iron oxide raw material fluid to be mixed between the processing surfaces, is introduced between the processing surfaces at the temperature of or higher than the normal boiling point of the iron oxide raw material fluid.

13. The method of producing an ultraviolet protective agent composition according to claim 11, comprising step (a-2) of performing an additional stirring treatment to the discharged fluid to be processed, after discharging the fluid to be processed from the space between the processing surfaces and before step (b).

14. The method of producing an ultraviolet protective agent composition according to claim 13, wherein pH of the fluid obtained in step (a-2) is 6 to 14.

15. The method of producing an ultraviolet protective agent composition according to claim 11, wherein pH of the discharged fluid in step (a) is 6 to 14.

16. The method of producing an ultraviolet protective agent composition according to claim 11, wherein the introduction pressure of both fluids to be processed of the iron oxide raw material fluid and the iron oxide precipitation fluid exceeds the standard pressure, and the temperature of the iron oxide raw material fluid to be introduced between the processing surfaces is higher than the normal boiling point of the iron oxide raw material fluid, and is lower than the boiling point under the introduction pressure.

17. The ultraviolet protective agent composition obtained by the method of producing an ultraviolet protective agent composition according to claim 5.

* * * * *